United States Patent [19]
Märkl et al.

[11] Patent Number: 5,889,012
[45] Date of Patent: Mar. 30, 1999

[54] SUBSTITUTED CYCLOALKYLAMINO AND CYCLOALKOXY HETEROCYCLES, PROCESSES FOR PREPARING THEM AND THEIR USE AS PESTICIDES

[75] Inventors: Martin Märkl, Frankfurt; Wolfgang Schaper, Diedorf; Werner Knauf, Eppstein; Ulrich Sanft, Hofheim; Manfred Kern, Lörzweiler; Werner Bonin, Kelkheim; Adolf Linkies, Frankurt; Dieter Bernd Reuschling, Butzbach, all of Germany

[73] Assignee: Hoechst-Schering AgrEvo GmbH, Berlin, Germany

[21] Appl. No.: 543,794

[22] Filed: Oct. 16, 1995

[30] Foreign Application Priority Data

Oct. 18, 1994 [DE] Germany .......... 44 37 137.3

[51] Int. Cl.$^6$ ............ C07D 239/34; C07D 239/38; C07D 239/42; C07D 31/505

[52] U.S. Cl. .......... 514/269; 544/319; 544/256; 544/324; 544/328; 544/327; 544/326; 544/278; 544/229; 544/295; 544/296; 544/238; 544/179; 544/180; 544/183; 544/280; 544/279; 544/284; 544/237; 544/264; 544/257; 514/63; 514/241; 514/242; 514/245; 514/252; 514/253; 514/254; 514/249

[58] Field of Search ............ 544/319, 326, 544/293, 287, 288, 253, 278, 324, 229, 238, 183, 284, 257; 514/256, 269, 258, 259; 540/481

[56] References Cited

U.S. PATENT DOCUMENTS

| | | |
|---|---|---|
| 4,615,727 | 10/1986 | Baltrüschat et al. .......... 71/93 |
| 5,441,960 | 8/1995 | Bernstein et al. .......... 514/269 |
| 5,510,343 | 4/1996 | Charnas et al. .......... 514/210 |
| 5,559,232 | 9/1996 | Ackermann et al. .......... 544/121 |
| 5,571,815 | 11/1996 | Schaper et al. .......... 544/319 |
| 5,574,024 | 11/1996 | Ebetino .......... 514/89 |
| 5,583,132 | 12/1996 | Vazquez et al. .......... 514/183 |

FOREIGN PATENT DOCUMENTS

| | | |
|---|---|---|
| 0 096 189 A2 | 10/1986 | European Pat. Off. . |
| 0 366 085 A2 | 10/1989 | European Pat. Off. . |
| 0 519 211 A1 | 5/1992 | European Pat. Off. . |
| 0519211 | 12/1992 | European Pat. Off. . |
| 42 08 254 | 9/1993 | Germany . |
| 93/19 050 A1 | 9/1993 | Germany . |
| WO 93/19050 | 9/1993 | WIPO . |
| WO 93/19050 | 9/1995 | WIPO . |

OTHER PUBLICATIONS

Grand & Hackh's, "Chemical Dictionary" 5th Edition (1987) p. 312.

*Primary Examiner*—John M. Ford
*Attorney, Agent, or Firm*—Frommer Lawrence & Huag LLP

[57] ABSTRACT

Substituted cycloalkylamino and cycloalkoxy heterocycles, processes for preparing them and their use as pesticides The invention relates to (I)

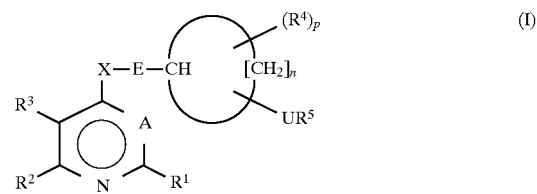

in which $R^1$ to $R^5$, A, X, E, U, p and n are as defined in claim 1, to processes for their preparation and their use as pesticides, such as insecticides, acaricides and fungicides.

12 Claims, No Drawings

SUBSTITUTED CYCLOALKYLAMINO AND CYCLOALKOXY HETEROCYCLES, PROCESSES FOR PREPARING THEM AND THEIR USE AS PESTICIDES

The invention relates to novel substituted cycloalkylamino and cycloalkoxy heterocycles, to processes for their preparation and to their use as pesticides and fungicides.

It is already known that certain cycloalkylamino and cycloalkoxyheterocycles exhibit a fungicidal, acaricidal and insecticidal action (DE-A-42 08 254). The biological action of these compounds, however, especially at low application rates and concentrations, is not satisfactory in every type of application.

Novel substituted cycloalkylamino and cycloalkoxy heterocycles have now been found of the general formula I

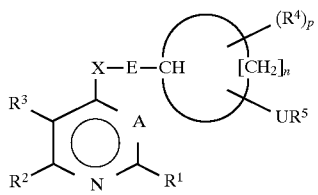

in which $R^1$ is hydrogen, halogen, $(C_1-C_4)$-alkyl, $(C_1-C_4)$-haloalkyl, $(C_3-C_5)$-cycloalkyl or halo-$(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_8)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or $R^2$ and $R^3$, together with the carbon atoms to which they are attached, form an unsaturated 5- or 6-membered isocyclic ring which, if it is a 5-membered ring, can contain an oxygen or sulfur atom in place of $CH_2$ or, if it is a 6-membered ring, can contain one or two nitrogen atoms in place of one or two CH units and which is unsubstituted or substituted by 1, 2 or 3 identical or different radicals which are $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$, together with the carbon atoms to which they are attached, form a saturated 5, 6- or 7-membered isocyclic ring which can contain oxygen and/or sulfur in place of one or two $CH_2$ groups and which is unsubstituted or substituted by 1, 2 or 3 $(C_1-C_4)$-alkyl groups;

A is CH or N;

X is NH, oxygen or $S(O)_q$ where q=0, 1 or 2;

E is a direct bond or a straight-chain or branched $(C_1-C_4)$-alkanediyl group, preferably a direct bond;

N is the integer 2, 3, 4, 5 or 6;

$(R^4)_p$ and $UR^5$ are substituents of the isocyclic ring formed with the participation of $[CH_2]_n$;

$R^4$ is hydrogen, halogen, alkyl, haloalkyl, alkoxy or alkylthio; and p is 1 or 2;

U is a direct bond, oxygen or a group $S(O)_m$ where m=0, 1 or 2;

$R^5$ is alkenyl if U is as defined above and A is nitrogen; or $R^5$ is alkenyl if U is as defined above, A is CH and $R^2$ and $R^3$, together with the carbon atoms to which they are attached, form an unsaturated ring; or $R^5$ is alkyl if U is a group $S(O)_m$ and A is as defined above; or $R^5$ is aryl or heterocyclyl if U is a group $S(O)_m$, m is 1 or 2 and A is as defined above; or $R^5$ is aryl or heterocyclyl if U is sulfur and A is CH; or $R^5$ is heterocyclyl if U is oxygen and A is nitrogen; or $R^5$ is aryl or heterocyclyl if U is oxygen and A is CH; or $R^5$ is heterocyclyl if U is a direct bond and A is CH; or $R^5$ is a haloalkyl group which if unsubstituted must contain more than 4 carbon atoms, if U is oxygen or a direct bond and A is nitrogen; or $R^5$ is a haloalkyl group which if unsubstituted must contain more than 4 carbon atoms, if U is oxygen or a direct bond, A is CH and $R^2$ and $R^3$, together with the carbon atoms to which they are attached, form an unsaturated ring; or $R^5$ if U and A are as defined above is alkynyl, hydroxyalkyl, cyanoalkyl, cyano, nitro, nitroalkyl, thiocyano, thiocyanoalkyl, cycloalkoxyalkyl, cycloalkylalkoxyalkyl, aryloxyalkyl, arylalkoxyalkyl, heterocyclyloxyalkyl, heterocyclylalkoxyalkyl, alkylmercaptoalkyl, cycloalkylmercaptoalkyl, cycloalkylalkylmercaptoalkyl, arylmercaptoalkyl, arylalkylmercaptoalkyl, heterocyclylmercaptoalkyl, heterocyclylalkylmercaptoalkyl, a group

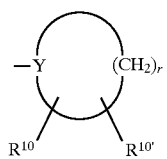

in which Y is carbon or silicon, r is an integer from 2 to 6 and $R^{10}$ and $R^{10'}$ are alkyl where, if Y is silicon, $R^{10}$ is preferably linked to Y; or is a group $R^6R^7R^8Si[(C_1-C_4)$-alkyl$]_s$ where s is zero or 1 and $R^6$ and $R^7$ are alkyl, preferably methyl, and $R^8$ is mono-, di- or trioxaalkyl or cycloalkyl-oxa-alkyl and, if s is 1, is also alkyl, cycloalkyl, aryl or arylalkyl;

in which the aryl and heterocyclyl radicals and the radicals derived therefrom which are listed can be unsubstituted or provided with up to 3 identical or different radicals or, in the case of fluorine, up to the maximum number, and in the alkyl, haloalkyl, alkenyl, alkynyl or $(R^6R^7R^8Si)$-alkyl radicals mentioned one or more, preferably up to three, nonadjacent saturated carbon units can be replaced by heteroatom units such as oxygen, $S(O)_x$ where x=0, 1 or 2, $NR^9$ or $SiR^{6'}R^{7'}$, where $R^9$ is hydrogen, $(C_1-C_4)$-alkyl, $(C_1-C_4)$-alkanoyl or $(C_1-C_4)$ -alkoxy and where R⁶' and R⁷' are $(C_1-C_4)$-alkyl, and in which, moreover, 3 to 12 atoms of these hydrocarbon or halogenated hydrocarbon radicals, unmodified or modified as above, can form a ring, and these hydrocarbon or halogenated hydrocarbon radicals, with or without the variations indicated can be unsubstituted or substituted with one or more, preferably up to three identical or different radicals, in the case of halogen up to the maximum number, said radicals being selected from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxy, cyano, thiocyano or nitro, where the cycloaliphatic, aromatic or heterocyclic ring systems of the substituents in this series can be unsubstituted or provided with up to three identical or different substituents, in the case of fluorine up to the maximum number, and salts thereof, preferably acid addition salts;

especially those compounds for which $R^5$ is $(C_2-C_{20})$-alkenyl if U is as defined above and A is nitrogen; or $R^5$ is $(C_2-C_{20})$-alkenyl if U is as defined above, A is CH and $R^2$ and $R^3$, together with the carbon atoms to which they are attached, form an unsaturated ring; or $R^5$ is $(C_1-C_{20})$-alkyl if U is a group $S(O)_m$ and A is as defined above; or $R^5$ is aryl or heterocyclyl if U is a group $S(O)_m$, m is 1 or 2 and A is as defined above; or $R^5$ is aryl or heterocyclyl if U is sulfur and A is CH; or $R^5$ is heterocyclyl if U is oxygen and A is nitrogen; or $R^5$ is aryl or heterocyclyl if U is oxygen and A is CH; or $R^5$ is heterocyclyl if U is a direct bond and A is CH; or $R^5$ is a $(C_1-C_{20})$-haloalkyl group which if unsubstituted must possess more than 4 carbon atoms, if U is oxygen or a direct bond and A is nitrogen; or $R^5$ is a $(C_1-C_{20})$-haloalkyl group which if unsubstituted must possess more than 4 carbon atoms, if U is oxygen or a direct bond, A is CH and $R^2$ and $R^3$, together with the carbon atoms to which they are attached, form an unsaturated ring; or $R^5$ if U and A are as defined above is $(C_2-C_{20})$-alkynyl, $(C_1-C_{20})$-hydroxyalkyl, $(C_1-C_{20})$-cyanoalkyl, cyano, nitro, $(C_1-C_{20})$-nitroalkyl, thiocyano, $(C_1-C_{20})$-thiocyanoalkyl, $(C_3-C_8)$-cycloalkoxy-$(C_1-C_4)$-alkyl, $(C_3-C_8)$-cycloalkyl-$(C_1-C_4)$-alkoxy-$(C_1-C_4)$-alkyl, aryloxy-$(Cl-C_4)$-alkyl, aryl-$(C_1-C_4)$-alkoxy-$(C_1-C_4)$-alkyl, heterocycloxy-$(C_1-C_4)$-alkyl, heterocyclyl-$(C_1-C_4)$-alkoxy-$(C_1-C_4)$-alkyl, $(C_1-C_8)$-alkylmercapto-$(C_1-C_4)$-alkyl, $(C_3-C_8)$-cycloalkylmercapto-$(C_1-C_4)$-alkyl, $(C_3-C_8)$-cycloalkyl-$(C_1-C_4)$-alkylmercapto-$(C_1-C_4)$-alkyl, arylmercapto-$(C_1-C_4)$-alkyl, aryl-$(C_1-C_4)$-alkylmercapto-$(C_1-C_4)$-alkyl, heterocyclylmercapto-$(C_1-C_4)$-alkyl, heterocyclyl-$(C_1-C_4)$-alkylmercapto-$(C_1-C_4)$-alkyl, a group

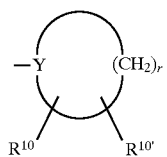

in which Y is carbon or silicon, r is an integer from 2 to 6 and $R^{10}$ and $R^{10'}$ are $(C_1-C_4)$-alkyl, in which, if Y is silicon, $R^{10}$ is preferably linked to Y; or is a group $R^6R^7R^8Si[(C_1-C_4)$-alkyl$]_s$, where s is zero or 1 and $R^6$ and $R^7$ are $(C_1-C_4)$-alkyl, preferably methyl, and $R^8$ is mono-, di- or trioxa-$(C_1-C_{20})$-alkyl or $(C_3-C_8)$-cycloalkyl-oxa-$(C_1-C_4)$-alkyl and, if s is 1, is also $(C_1-C_8)$-alkyl, $(C_3-C_8)$-cycloalkyl, aryl or aryl-$(C_1-C_4)$-alkyl;

in which the aryl and heterocyclyl radicals and the radicals derived therefrom which are listed can be unsubstituted or provided with up to 3 identical or different radicals, or in the case of fluorine up to the maximum number and in the alkyl, haloalkyl, alkenyl, alkynyl or $(R^6R^7R^8Si)$-alkyl radicals mentioned, one or more, preferably up to three, nonadjacent saturated carbon units can be replaced by heteroatom units such as oxygen, $S(O)_x$ where x=0, 1 or 2, $NR^9$ or $SiR^6R^7'$, in which $R^9$ is hydrogen $(C_1-C_4)$-alkyl, $(C_1-C_4)$-alkanoyl or $(C_1-C_4)$-alkoxy, and where $R^6'$ and $R^7'$ are $(C_1-C_4)$-alkyl, and in which, moreover, 3 to 12 atoms of these hydrocarbon radicals or halogenated hydrocarbon radicals which are unmodified or are modified as above can form a ring and these hydrocarbon or halogenated hydrocarbon radicals, with or without the variations indicated can be unsubstituted or substituted with one or more, preferably up to three, identical or different radicals, in the case of halogen up to the maximum number, said radicals being selected from the series consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, where the cycloaliphatic, aromatic or heterocyclic ring systems among this series can be unsubstituted or provided with up to three identical or different substituents, and in the case of fluorine up to the maximum number, and, moreover, the groups —X—E— and $UR^5$, if n is 5 and the system is therefore a cyclohexane system, are cis to one another and take up positions 1 and 4.

Preferred compounds of the formula I are those in which $R^1$ is hydrogen, chlorine or fluorine;

$R^2$ is $(C_1-C_4)$-alkyl, $(C_1-C_4)$-haloalkyl, cyclopropyl, halocyclopropyl, $(C_2-C_4)$-alkenyl, $(C_2-C_4)$- haloalkenyl, $(C_2-C_4)$-alkynyl, trimethylsilylethynyl, methoxymethyl or cyano;

$R^3$ is hydrogen, halogen, methyl, ethyl, $(C_2-C_4)$-alkenyl, $(C_2-C_4)$-haloalkenyl, $(C_2-C_4)$-alkynyl, trimethylsilylethynyl, methoxy, ethoxy, cyano or $(C_1-C_4)$-alkoxycarbonyl; or $R^2$ and $R^3$, together with the carbon atoms to which they are attached, form an unsubstituted or substituted unsaturated 5- or 6-membered ring which, if it is a 5-membered ring, can contain a sulfur atom in place of a $CH_2$ unit; or $R^2$ and $R^3$, together with the carbon atoms to which they are attached, form a saturated 5- or 6-membered ring which can contain a sulfur atom or an oxygen atom in place of a $CH_2$ unit;

A is CH or N;

X is NH or oxygen;

E is a direct bond;

n is the number 5;

$R^4$ is hydrogen, $(C_1-C_4)$-alkyl, trifluoromethyl or $(C_1-C_4)$-alkoxy; and, in addition, the groups —X—E— and $UR^5$, if n is 5 and the system is therefore a cyclohexane system, are cis to one another and take up positions 1 and 4;

especially those compounds in which $R^1$ is hydrogen or fluorine, $R^2$ is methyl, ethyl, propyl, isopropyl, $(C_1-C_2)$-fluoroalkyl, ethynyl, trimethylsilylethynyl, cyclopropyl or methoxymethyl;

$R^3$ is halogen, methyl, ethyl, ethynyl, trimethylsilylethynyl, methoxy, ethoxy or cyano; or $R^2$ and $R^3$, together with the ring system to which they are attached, form the quinazoline or quinoline system which can be substituted in the carbocyclic part by fluorine; or $R^2$ and $R^3$, together with the carbon atoms to which they are attached, form a saturated 6-membered ring which can contain an oxygen atom or sulfur atom in place of a $CH_2$ group; and $R^4$ is hydrogen, methyl or trifluoromethyl.

Particularly preferred compounds of the formula I are those in which $R^1$ is hydrogen;

$R^2$ is ethyl, propyl, isopropyl, trifluoromethyl, 1-fluoroethyl, ethynyl, trimethylsilylethynyl or methoxymethyl;

$R^3$ is fluorine, chlorine, bromine, ethynyl, trimethylsilylethynyl or methoxy; or, if A is nitrogen, $R^2$ and $R^3$, together with the ring system to which they are attached, form the quinazoline system which can be substituted with a fluorine atom; or $R^2$ and $R^3$, together with the ring system to which they are attached, form the 5,6,7,8-tetrahydroquinazoline system;

A is CH or N;

X is NH or oxygen;

E is a direct bond;

$R^4$ is hydrogen or methyl;

n is the number 5; and, in addition, the groups —X—E— and $UR^5$, if n is 5 and the system is therefore a cyclohexane system, are cis to one another and take up positions 1 and 4.

The most preferred compounds of the formula I are those in which $R^1$ is hydrogen;

$R^2$ is ethyl or methoxymethyl;

$R^3$ is fluorine, chlorine, bromine or methoxy; or $R^2$ and $R^3$, together with the ring system to which they are attached, form the quinazoline or 5,6,7,8-tetrahydroquinazoline system;

A is CH or N;

X is NH or oxygen;

E is a direct bond;

$R^4$ is hydrogen;

n is the number 5;

U is a direct bond; and, in addition, the groups —X—E— and $UR^5$, if n is 5 and the system is therefore a cyclohexane system, are cis to one another and take up positions 1 and 4;

especially those in which $R^2$ is methoxymethyl and $R^3$ is methoxy, or $R^2$ is ethyl and $R^3$ is chlorine or bromine;

X is NH;

A is nitrogen; and salts thereof, preferably acid addition salts.

In the above definitions, halogen means a fluorine, chlorine, bromine or iodine atom;

$(C_1-C_4)$-alkyl means an unbranched or branched hydrocarbon radical having 1 to 4 carbon atoms, such as the methyl, ethyl, propyl, isopropyl, 1-butyl, 2-butyl, 2-methylpropyl or tert-butyl radical;

$(C_1-C_8)$-alkyl means the abovementioned alkyl radicals and, for example, the pentyl, 2-methylbutyl, 1,1-dimethylpropyl, hexyl, heptyl, octyl, or 1,1,3,3-tetramethylbutyl radical;

$(C_1-C_{20})$-alkyl means the abovementioned alkyl radicals and, for example, the nonyl, 1-decyl, 2-decyl, undecyl, dodecyl, pentadecyl or eicosyl radical;

$(C_1-C_4)$-haloalkyl means an alkyl group as for $(C_1-C_4)$-alkyl in which one or more hydrogen atoms are replaced by the abovementioned halogen atoms, preferably chlorine or fluorine, for example the trifluoromethyl group, the 1-fluoroethyl group, the 2,2,2-trifluoroethyl group, the chloromethyl group, the fluoromethyl group, the difluoromethyl group or the 1,1,2,2-tetrafluoroethyl group;

$(C_1-C_2)$-fluoroalkyl means for example the mono-, di- or trifluoromethyl group or the 1-fluoroethyl, 2-fluoroethyl, 1,1-difluoroethyl, 2,2,2-trifluoroethyl or pentafluoroethyl group;

a haloalkyl group which if unsubstituted must possess more than 4 carbon atoms means a $(C_5-C_{20})$-alkyl group in which one or more hydrogen atoms, and in the case of fluorine up to the maximum number, are replaced by the abovementioned halogen atoms, preferably chlorine or fluorine, for example the perfluoropentyl, perfluorohexyl, perfluoroheptyl or perfluorooctyl group or the 1H, 1H-perfluoroheptyl, 1H,1H,2H,2H-perfluorohexyl, 1H,1H,2H,2H-perfluorooctyl or 1H,1H-perfluorooctyl group, but also a $(C_1-C_4)$-alkyl group in which one or more hydrogen atoms are replaced by one of the abovementioned radicals and in which, in addition, one or more hydrogen atoms, and in the case of fluorine up to the maximum number, are replaced by halogen atoms, preferably chlorine or fluorine, for example the 1,1,1-trifluoro-2-hydroxy-2-propyl group;

cycloalkyl means preferably $(C_3-C_8)$-cycloalkyl;

cycloalkoxy means preferably $(C_3-C_8)$-cycloalkoxy;

cycloalkylthio means preferably $(C_3-C_8)$-cycloalkylthio;

$(C_3-C_5)$-cycloalkyl means the cyclopropyl, cyclobutyl or cyclopentyl group;

$(C_3-C_8)$-cycloalkyl means the radicals mentioned above under $(C_3-C_5)$-cycloalkyl and also the cyclohexyl, cycloheptyl or cyclooctyl radical, and also bicyclic systems such as the norbornyl group or the bicyclo[2.2.2]octane radical;

$(C_3-C_5)$-halocycloalkyl means one of the abovementioned $(C_3-C_5)$-cycloalkyl radicals in which one or more hydrogen atoms, or in the case of fluorine possibly all the hydrogen atoms, are replaced by halogen, preferably fluorine or chlorine, for example the 2,2-difluoro- or 2,2-dichlorocyclopropane group or the fluorocyclopentane radical;

$(C_2-C_4)$-alkenyl means for example the vinyl, allyl, 2-methyl-2-propenyl or 2-butenyl group;

$(C_2-C_{20})$-alkenyl means the abovementioned radicals and for example the 2-pentynyl, 2-decenyl or 2-eicosenyl group;

$(C_2-C_4)$-haloalkenyl means a $(C_2-C_4)$-alkenyl group in which some or alternatively, in the case of fluorine, all of the hydrogen atoms are replaced by halogen, preferably fluorine or chlorine;

$(C_2-C_4)$-alkynyl means for example the ethynyl, propargyl, 2-methyl-2-propynyl or 2-butynyl group;

$(C_2-C_{20})$-alkynyl means the abovementioned radicals and for example the 2-pentynyl or 2-decynyl group;

$(C_2-C_4)$-haloalkynyl means a $(C_2-C_4)$-alkynyl group in which some or alternatively, in the case of fluorine, all of the hydrogen atoms are replaced by halogen atoms, preferably fluorine or chlorine;

tri-$(C_1-C_4)$-alkylsilyl-$(C_2-C_4)$-alkynyl means preferably the trimethylsilylethynyl group;

$(C_1-C_4)$-hydroxyalkyl means for example the hydroxymethyl, 1-hydroxyethyl, 2-hydroxyethyl, 1-hydroxy-1-methylethyl or 1-hydroxypropyl group;

$(C_1-C_4)$-alkanoyl means for example the formyl, acetyl, propionyl, 2-methylpropionyl or butyryl group;

$(C_1-C_{12})$-alkanoyl means for example the abovementioned radicals and, for example, the valeroyl, pivaloyl, hexanoyl, decanoyl or dodecanoyl group;

$(C_2-C_4)$-haloalkanoyl means a $(C_1-C_4)$-alkanoyl group in which some or alternatively, in the case of fluorine, all of the hydrogen atoms are replaced by halogen atoms, preferably fluorine or chlorine;

$(C_2-C_{12})$-haloalkanoyl means a $(C_1-C_{20})$-alkanoyl group in which some or alternatively, in the case of fluorine, all of the hydrogen atoms are replaced by halogen atoms, preferably fluorine or chlorine;

cyano-$(C_1-C_4)$-alkyl means a cyanoalkyl group whose hydrocarbon radical is as defined for $(C_1-C_4)$-alkyl;

$(C_1-C_4)$-alkoxycarbonyl means for example the methoxycarbonyl, ethoxycarbonyl, propoxycarbonyl, butoxycarbonyl or tert-butoxycarbonyl group;

$(C_1-C_{12})$-alkoxycarbonyl means the abovementioned radicals and for example the hexyloxycarbonyl, 2-methylhexyloxycarbonyl, decyloxycarbonyl or dodecyloxycarbonyl group;

$(C_1-C_4)$-haloalkoxycarbonyl means a $(C_1-C_4)$-alkoxycarbonyl group in which one or more hydrogen atoms, and in the case of fluorine possibly all the hydrogen atoms, are replaced by halogen, preferably fluorine or chlorine;

$(C_1-C_4)$-alkylthio means an alkylthio group whose hydrocarbon radical is as defined for $(C_1-C_4)$-alkyl;

$(C_1-C_4)$-haloalkylthio means a $(C_1-C_4)$-alkylthio group in which one or more hydrogen atoms, and in the case of fluorine possibly all the hydrogen atoms, of the hydrocarbon part are replaced by halogen, especially chlorine or fluorine;

fluoromethylthio means the mono-, di- or trifluoromethylthio group;

$(C_1-C_4)$-alkylsulfinyl means for example the methyl-, ethyl-, propyl-, isopropyl-, butyl-, isobutyl-, sec-butyl- or tert-butylsulfinyl group; $(C_1-C_4)$-alkylsulfonyl means for example the methyl-, ethyl-, propyl-, isopropyl-, butyl-, isobutyl-, sec-butyl- or tert-butylsulfonyl group;

$(C_1-C_4)$-haloalkylsulfinyl and $(C_1-C_4)$-haloalkylsulfonyl means $(C_1-C_4)$-alkylsulfinyl and -sulfonyl radicals as defined above in which one or more hydrogen atoms, and in the case of fluorine possibly all the hydrogen atoms, of the hydrocarbon part are replaced by halogen, especially chlorine or fluorine;

fluoromethylsulfinyl and fluoromethylsulfonyl mean the mono-, di- or trifluoromethyl-sulfinyl or -sulfonyl group;

$(C_1-C_4)$-alkoxy means an alkoxy group whose hydrocarbon radical is as defined for $(C_1-C_4)$-alkyl;

$(C_1-C_4)$-haloalkoxy means a haloalkoxy group whose halogenated hydrocarbon radical is as defined for $(C_1-C_4)$-haloalkyl;

$(C_1-C_4)$-alkoxy-$(C_1-C_4)$-alkyl means for example a 1-methoxyethyl group, a 2-methoxyethyl group, a 2-ethoxyethyl group, a methoxymethyl group or an ethoxymethyl group, a 3-methoxypropyl group or a 4-butoxybutyl group;

$(C_1-C_4)$-haloalkoxy-$(C_1-C_4)$-alkyl, $(C_1-C_4)$-alkoxy-$(C_1-C_4)$-haloalkyl and $(C_1-C_4)$-haloalkoxy-$(C_1-C_4)$-haloalkyl mean $(C_1-C_4)$-alkoxy-$(C_1-C_4)$-alkyl radicals as defined above in which one or more hydrogen atoms, and in the case of fluorine possibly all the hydrogen atoms, of the corresponding hydrocarbon moieties are replaced by halogen, preferably chlorine or fluorine;

$(C_1-C_4)$-alkylthio-$(C_1-C_4)$-alkyl means for example methylthiomethyl, ethylthiomethyl, propylthiomethyl, 2-methylthioethyl, 2-ethylthioethyl or 3-methylthiopropyl;

aryl means an isocyclic aromatic radical having preferably 6 to 14, especially 6 to 12, carbon atoms, for example phenyl, naphthyl or biphenylyl, preferably phenyl;

heterocyclyl means a heteroaromatic or heteroaliphatic ring system, where heteroaromatic ring system means an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and heteroaliphatic ring system means a $(C_3-C_8)$-cycloalkyl radical in which at least one carbon unit is replaced by O, S or a group $NR^{11}$ and $R^{11}$ is hydrogen, $(C_1-C_4)$-alkyl, $(C_1-C_4)$-alkoxy or aryl;

arylthio means for example the phenylthio group or the 1- or 2-naphthylthio group;

aryloxy means for example the phenoxy group or the 1- or 2-naphthyloxy group;

heterocyclyloxy or heterocyclylthio means one of the abovementioned heterocyclic radicals which are linked via an oxygen atom or sulfur atom;

$(C_3-C_8)$-cycloalkoxy or $(C_3-C_8)$-cycloalkylthio means one of the abovementioned $(C_3-C_8)$-cycloalkyl radicals which are linked via an oxygen atom or sulfur atom;

aroyl means for example the benzoyl, naphthoyl or biphenylcarbonyl group;

aryl-$(C_1-C_4)$-alkanoyl means for example the phenylacetyl, 3-phenylpropionyl, 2-phenylpropionyl, 2-methyl-2-phenylpropionyl, 4-phenylbutyryl or naphthylacetyl group;

$(C_3-C_8)$-cycloalkyl-$(C_1-C_4)$-alkanoyl means for example the cyclopropylcarbonyl, cyclobutylcarbonyl, cyclopentylcarbonyl, cyclohexylcarbonyl, cyclohexylacetyl or cyclohexylbutyryl group;

heterocyclyl-$(C_1-C_4)$-alkanoyl means for example the thenoyl, furoyl, nicotinoyl, thienylacetyl or pyridinepropionyl group;

$(C_3-C_8)$-cycloalkoxycarbonyl means for example the cyclobutyloxycarbonyl, cyclopentyloxycarbonyl, cyclohexyloxycarbonyl or cycloheptyloxycarbonyl group;

$(C_3-C_8)$-cycloalkyl-$(C_1-C_4)$-alkoxycarbonyl means for example the cyclopropylmethoxycarbonyl, cyclobutylmethoxycarbonyl, cyclopentylmethoxycarbonyl, cyclohexylmethoxycarbonyl, 1-(cyclohexyl)-ethoxycarbonyl or 2-(cyclohexyl)-ethoxycarbonyl group;

aryl-$(C_1-C_4)$-alkoxycarbonyl means for example the benzyloxycarbonyl, 1-naphthylmethoxycarbonyl, 2-naphthylmethoxycarbonyl, 1-phenylethoxycarbonyl or 2-phenylethoxycarbonyl group;

heterocyclyl-$(C_1-C_4)$-alkoxycarbonyl means for example the thienylmethoxycarbonyl, furylmethoxycarbonyl, tetrahydrofurylmethoxycarbonyl or pyridylethoxycarbonyl group;

aryloxycarbonyl means for example the phenoxycarbonyl, naphthoxycarbonyl or biphenyloxycarbonyl group;

heterocyclyloxycarbonyl means for example the tetrahydropyran-4-oxycarbonyl group;

$(C_1-C_{20})$-alkanoyloxy means for example the formyloxy, acetoxy, propionyloxy, butyryloxy, pivaloyloxy, valeroyloxy or hexanoyloxy group;

$(C_2-C_{20})$-haloalkanoyloxy means a $(C_2-C_{20})$-alkanoyloxy group in which one or more hydrogen atoms, and in the case of fluorine possibly all the hydrogen atoms, of the hydrocarbon part are replaced by halogen, especially fluorine or chlorine;

$(C_3-C_8)$-cycloalkanoyloxy means for example the cyclopropanoyloxy, cyclobutanoyloxy, cyclopentanoyloxy, cyclohexanoyloxy or cycloheptanoyloxy group;

$(C_3-C_8)$-cycloalkyl-$(C_1-C_4)$-alkanoyloxy means for example the cyclopropylcarbonyloxy, cyclopropylacetoxy, cyclobutylcarbonyloxy, cyclopentylcarbonyloxy, cyclohexylcarbonyloxy, cyclohexylacetoxy or 4-cyclohexylbutyryloxy group;

aroyloxy means for example the benzoyloxy or naphthoyloxy group;

aryl-$(C_1-C_4)$-alkanoyloxy means for example the benzoyloxy, naphthoyloxy, biphenylcarbonyloxy, phenylacetoxy or phenylbutyryloxy group;

heterocyclyl-$(C_1-C_4)$-alkanoyloxy means for example the thienylcarbonyloxy, thienylacetoxy, pyridylcarbonyloxy or pyrimidinylcarbonyloxy group;

$(C_1-C_{20})$-alkylsulfonyloxy means for example the methane-, ethane-, butane- or hexanesulfonyl group;

arylsulfonyloxy means for example the phenylsulfonyloxy or toluenesulfonyloxy group;

nitro-$(C_1-C_{20})$-alkyl means a nitroalkyl group whose hydrocarbon radical is as defined for $(C_1-C_{20})$-alkyl;

thiocyano-$(C_1-C_{20})$-alkyl means a thiocyanoalkyl group whose hydrocarbon radical is as defined for $(C_1-C_{20})$-alkyl;

$(C_1-C_{20})$-hydroxyalkyl means a hydroxyalkyl group whose hydrocarbon radical is as defined for $(C_1-C_{20})$-alkyl;

$(C_1-C_{20})$-cyanoalkyl means a cyanoalkyl group whose hydrocarbon radical is as defined for $(C_1-C_{20})$-alkyl;

a group

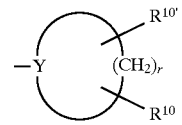

in which Y is carbon or silicon, r is the number 2, 3, 4, 5 or 6 and $R^{10}$ and $R^{10'}$ are $(C_1-C_4)$-alkyl is for example the 1-methylcyclopropyl, -cyclobutyl, -cyclopentyl or -cyclohexyl group, the 1-methyl-1-sila-cyclopentyl or 1-methyl-1-sila-cyclohexyl group;

a group $R6R^7R^8Si[(C_1-C_4)\text{-alkyl}]_s$ where s is zero, $R^6$ and $R^7$ are preferably methyl and $R^8$ is mono-, di- or trioxa-$(C_1-C_{20})$-alkyl is for example the dimethyl-(2-ethoxyethyl)-silyl group, the dimethyl-(3-ethoxypropyl)-silyl group, the dimethyl-[3-(2-methoxyethoxy)propyl]-silyl group, the dimethyl-[3-(2-ethoxy)propyl]-silyl group, the dimethyl(3-butoxypropyl)-silyl group, the dimethyl-[3-[2-(2-ethoxyethoxy)ethoxy]propyl]-silyl group, or the dimethylmethoxy- or -ethoxy-methyl-silyl group;

a group $R^6R^7R^8Si[(C_1-C_4)\text{-alkyl}]_s$ in which s is zero, $R^6$ and $R^7$ are preferably methyl and $R^8$ is $(C_3-C_8)$-cycloalkyl-oxa-$(C_1-C_4)$-alkyl is for example the dimethyl-(3-cyclohexyloxypropyl)-silyl group or the dimethyl-(2-cyclohexyloxyethyl)-silyl group;

a group $R^6R^7R^8Si[(C_1-C_4)\text{alkyl}]_s$ in which s is 1, $R^6$ and $R^7$ are preferably methyl and $R^8$ is $(C_1-C_{20})$-alkyl, ($C_3$–$C_8$)-cycloalkyl, aryl or aryl-($C_1$–$C_4$)-alkyl is for example the trimethylsilylmethyl or trimethylsilylethyl group, the dimethylbutlsilylmethyl or dimethylbutylsilylethyl group, the dimethyloctylsilylmethyl or dimethyloctylsilylethyl group, the dimethylcyclopentylsilylmethyl or dimethylcyclopentylsilylethyl group, the dimethylcyclohexylsilylmethyl or dimethylcyclohexylsilylethyl group, or the dimethylphenylsilylmethyl or dimethylphenylsilylethyl group;

($C_3$–$C_8$)-cycloalkoxy-($C_1$–$C_4$)-alkyl means for example the cyclohexyloxymethyl or cyclohexyloxyethyl group;

($C_3$–$C_8$)-cycloalkyl-($C_1$–$C_4$)-alkoxy-($C_1$–$C_4$)-alkyl means for example the cyclohexylmethoxymethyl or cyclopropylmethoxymethyl group;

aryloxy-($C_1$–$C_4$)-alkyl means for example the phenoxymethyl, phenoxyethyl, naphthoxymethyl or biphenyloxymethyl group;

aryl-($C_1$–$C_4$)-alkoxy-($C_1$–$C_4$)-alkyl means for example the benzyloxymethyl, naphthylmethoxymethyl, benzyloxyethyl or biphenylmethoxymethyl group;

heterocyclyloxy-($C_1$–$C_4$)-alkyl means for example the pyridyloxymethyl, pyrimidinyloxymethyl, quinolyloxymethyl or isoquinolyloxymethyl group;

heterocyclyl-($C_1$–$C_4$)-alkoxy-($C_1$–$C_4$)-alkyl means for example the thienylmethoxymethyl, furfuryloxymethyl or pyridylmethoxymethyl group;

($C_1$–$C_8$)-alkylmercapto-($C_1$–$C_4$)-alkyl means for example the methylthiomethyl, methylthioethyl, ethylthiomethyl, tert-butylthiomethyl, hexylthiomethyl or octylthiomethyl group;

($C_3$–$C_8$)-cycloalkylmercapto-($C_1$–$C_4$)-alkyl means for example the cyclohexyl- or cyclopentylthiomethyl group;

($C_3$–$C_8$)-cycloalkyl-($C_1$–$C_4$)-alkylmercapto-($C_1$–$C_4$)-alkyl means for example a cyclohexylmethylthiomethyl or -ethyl group;

heterocyclylmercapto-($C_1$–$C_4$)-alkyl means for example the pyridylthiomethyl, pyridylthioethyl, pyrimidylthiomethyl or pyridazinylthiomethyl group;

arylmercapto-($C_1$–$C_4$)-alkyl means for example the phenylthiomethyl, phenylthioethyl, naphthylthiomethyl or biphenylthiomethyl group;

aryl-($C_1$–$C_4$)-alkylmercapto-($C_1$–$C_4$)-alkyl means for example the benzylthiomethyl, benzylthioethyl or naphthylthiomethyl group;

heterocyclyl-($C_1$–$C_4$)-alkylmercapto-($C_1$–$C_4$)-alkyl means for example the thienylmethylthiomethyl, furfurylthiomethyl, tetrahydrofurfurylthiomethyl or pyridylmethylthiomethyl group.

The substituents with which the various aliphatic, aromatic and heterocyclic ring systems can be provided include for example halogen, nitro, cyano, di-($C_1$–$C_4$)-alkylamino, ($C_1$–$C_4$)-alkyl, ($C_3$–$C_8$)-cycloalkyl, ($C_1$–$C_4$)-trialkylsilyl, ($C_1$–$C_4$)-alkoxy, ($C_1$–$C_4$)-alkoxy-($C_1$–$C_4$)-alkyl, ($C_1$–$C_2$)-alkoxy-[$CH_2CH_2O$]$_{1,2}$-ethoxy, ($C_1$–$C_4$)-alkylthio, ($C_1$–$C_4$)-alkylsulfinyl, ($C_1$–$C_4$)-alkylsulfonyl, thiocyano, ($C_1$–$C_4$)-haloalkyl, ($C_1$–$C_4$)-haloalkoxy, ($C_1$–$C_4$)-haloalkylthio, ($C_2$–$C_4$)-haloalkylsulfinyl, ($C_1$–$C_4$)-haloalkylsulfonyl, ($C_2$–$C_4$)-alkenyl, ($C_2$–$C_4$)-haloalkenyl, trimethylsilylethynyl, ($C_1$–$C_4$)-alkanoyl, ($C_1$–$C_4$)-alkoxycarbonyl, phenyl, benzyl, phenoxy, halophenoxy, ($C_1$–$C_4$)-alkylphenoxy, ($C_1$–$C_4$)-alkoxyphenoxy, phenylthio, heterocyclyl, heterocyclylthio or heterocyclyloxy, where in the alkyl radicals and the radicals derived therefrom one or more hydrogen atoms, and in the case of fluorine up to the maximum number, can be replaced by halogen, preferably chlorine or fluorine, and if these substituents are ($C_1$–$C_4$)-alkyl, they can also be cyclically linked and, in these condensed ring systems such as the indane, dihydroxynaphthyl, tetrahydronaphthyl or benzocycloheptane system, one or two aliphatic carbon units can be replaced by heteroatom units such as oxygen or sulfur and, on the aliphatic carbon atom units, one or more hydrogen atoms, and in the case of fluorine up to the maximum number, can be replaced by halogen or ($C_1$–$C_4$)-alkyl.

Furthermore, the definition that "in the alkyl, haloalkyl, alkenyl, alkynyl or ($R^6R^7R^8Si$)-alkyl radicals mentioned one or more, preferably up to three, nonadjacent saturated carbon units can be replaced by a carbonyl group or by heteroatom units such as oxygen, $S(O)_x$ where $x=0$, 1 or 2, $NR^6$ or $SiR^7R^8$, where $R^6$ is hydrogen, ($C_1$–$C_4$)-alkyl, ($C_1$–$C_4$)-alkoxy or ($C_1$–$C_4$)-alkanoyl and where $R^7$ and $R^8$ are ($C_1$–$C_4$)-alkyl, preferably methyl, and in which, moreover, 3 to 12 atoms of these hydrocarbon radicals, unmodified or modified as above, can form a ring, and these hydrocarbon radicals, with or without the variations indicated can be unsubstituted or substituted with one or more, preferably up to three identical or different radicals, in the case of halogen up to the maximum number, said radicals being selected from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxy, cyano, thiocyano or nitro, where the cycloaliphatic, aromatic or heterocyclic ring systems of the substituents in this series can be unsubstituted or provided with up to three identical or different substituents, in the case of fluorine up to the maximum number", there are to be understood, for example:

alkoxyalkyl radicals such as the methoxymethyl, methoxyethyl or ethoxyethyl group; or alkoxyalkoxyalkyl radicals, such as the methoxy- or the ethoxy-ethoxyethyl group; or alkylthioalkyl radicals such as the methyl- or the ethylthioethyl group; or alkylsulfinyl alkyl radicals such as the methyl- or ethylsulfinylethyl group; or alkylsulfonylalkyl radicals such as the methyl- or ethylsulfonylethyl group; or alkyldialkylsilylalkyl, preferably alkyldimethylsilylalkyl radicals, such as the trimethylsilylmethyl or trimethylsilylethyl group; or trialkylsilyl radicals, preferably alkyldimethylsilyl radicals, such as the trimethylsilyl, ethyldimethylsilyl, tert-butyidimethylsilyl or octyidimethylsilyl group; or cycloalkyidialkylsilyl radicals, preferably cycloalkyldimethylsilyl radicals, such as the cyclohexyldimethylsilyl group; or aryldialkylsilyl radicals, preferably aryldimethylsilyl radicals, such as the phenyldimethylsilyl group; or arylalkyldialkylsilyl radicals, preferably aryldimethylsilyl radicals, such as the benzyldimethylsilyl or phenylethyldimethylsilyl group; or alkanoylalkyl radicals, such as the acetylmethyl or pivaloylmethyl group; or cycloalkanoyl alkyl radicals, such as the cyclopropylcarbonylmethyl or cyclohexylcarbonylmethyl group; or haloalkanoylalkyl radicals such as the trifluoro- or trichloroacetylmethyl group; or aroylalkyl radicals such as the benzoyl- or naphthoylalkyl radicals, for example the phenylacetylmethyl group; or heterocyclylcarbonyl alkyl radicals such as the thienyl- or pyridylacetylmethyl group; or arylalkyl radicals, such as the benzyl, 2-phenylethyl, 1-phenylethyl, 1-methyl-1-phenylethyl, 3-phenylpropyl, 4-phenylbutyl, 2-methyl-2-phenylethyl or 1-methylnaphthyl or 2-methylnaphthyl group; or heterocyclylalkyl radicals, such as the thienylmethyl, pyridylmethyl, furfuryl, tetrahydrofurfuryl, tetrahydropyranylmethyl or 1,3-dioxolane-2-methyl group; or aryloxyalkyl radicals such as the phenoxymethyl or naphthoxymethyl group; or cycloalkyl radicals, monocyclic such as the cyclopropyl, cyclobutyl, cyclopentyl, cyclohexyl, cycloheptyl or cyclooctyl radical, bicyclic such as the norbornyl radical or the bicyclo[2.2.2]octane radical or condensed such as the decahydronaphthyl radical;

alkylcycloalkyl radicals such as the 4-methyl- or 4-tert-butyl cyclohexyl group or the 1-methylcyclopropyl, -cyclobutyl, -cyclopentyl or -cyclohexyl group;

cycloalkylalkyl radicals such as the cyclohexylmethyl or cyclohexylethyl group;

or alternatively haloalkyl derivatives of the corresponding groups, such as, for example, haloalkyl, haloalkoxyalkyl, alkoxyhaloalkyl, haloalkylcycloalkyl or halocycloalkyl radicals;

or haloalkenyl radicals such as the 1- or 2-fluorovinyl group, 1- or 2-chlorovinyl group, 1- or 2-bromovinyl group, 1- or 2-trifluorovinyl group or 1- or 2-fluoropropenyl group.

The explanation given above applies correspondingly to homologs and to their derived radicals.

The present invention relates to the compounds of the formula I in the form of the free base or of an acid addition salt. Acids which can be used for forming salts are inorganic acids such as hydrochloric acid, hydrobromic acid, nitric acid, sulfuric acid and phosphoric acid or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In addition to the cis/trans isomerism of the cycloalkyl group, as mentioned, some of the compounds of the formula I have one or more asymmetric carbon atoms or stereoisomers at double bonds. It is therefore possible for enantiomers or diastereomers to occur. The invention comprises both the pure isomers and mixtures thereof. The mixtures of diastereomers can be resolved into the components by conventional methods, for example by selective crystallization from suitable solvents or by chromatography. Racemates can be resolved into the enantiomers by conventional methods, for example by forming salts with an optically active acid, separating the diastereomeric salts and liberating the pure enantiomers by means of a base.

The invention also relates to a process for the preparation of compounds of the formula 1, which comprises reacting a compound of the formula 11

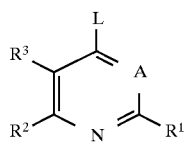

in which A, $R^1$, $R^2$ and $R^3$ are as defined under formula I and L is a leaving group, for example halogen, alkylthio, alkanesulfonyloxy or arylsulfonyloxy, alkylsulfonyl or arylsulfonyl with a nucleophile of the formula III

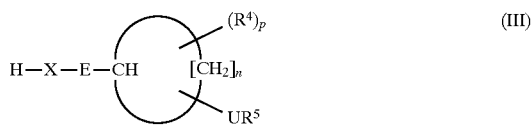

in which X, E, U, n, p, $R^4$ and $R^5$ are as defined under formula I above, and subjecting the compounds of the formula I obtained in this way or in another way to further derivatization, if desired, on the heterocycle or in the side chain $R^5$.

The substitution reaction described above is known in principle. The leaving group L can be varied within broad limits and can for example be a halogen atom such as fluorine, chlorine, bromine or iodine, or alkylthio such as methylthio or ethylthio, or alkanesulfonyloxy such as methane-, trifluoromethane- or ethanesulfonyloxy, or arylsulfonyloxy such as benzenesulfonyloxy or toluenesulfonyloxy, or alkylsulfonyl such as methylsulfonyl or ethylsulfonyl, or arylsulfonyl such as phenylsulfonyl or toluenesulfonyl.

The abovementioned reaction is carried out in a temperature range from 20° to 150° C., expediently in the presence of a base and, if desired, in an inert organic solvent such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. It is also possible to use mixtures of the solvents mentioned.

Suitable bases for the case in which X is oxygen are for example alkali metal or alkaline earth metal carbonates, hydrogen carbonates, amides or hydrides, such as sodium carbonate, sodium hydrogen carbonate, potassium carbonate, sodium amide or sodium hydride, and for the case in which X is NH they are, for example, alkali metal or alkaline earth metal carbonates, hydrogen carbonates, hydroxides, amides or hydrides, such as sodium carbonate, sodium hydrogen carbonate, potassium carbonate, sodium hydroxide, sodium amide or sodium hydride, or organic bases such as triethylamine or pyridine. A second equivalent of an amine of the formula III can also be employed as auxiliary base.

When X is oxygen, the nucleophiles of the formula III required as starting materials can be prepared by known methods, for example by reducing a carbonyl group using an appropriate reducing agent, for example a complex metal hydride, or, in the case of an aldehyde or ketone, with hydrogen and a hydrogenation catalyst. For the preparation of the cis-cyclohexanols, the starting materials for the particularly preferred cis-cyclohexyloxy derivatives, particularly suitable methods are the catalytic hydrogenation of suitably substituted phenols or the reduction of suitably substituted cyclohexanone derivatives with complex hydrides which carry spatially bulky substituents, for example L-Selectride®.

When X is NH, the nucleophiles of the formula III required as starting materials can be prepared by known methods, for example by reducing an oxime or a nitrile using an appropriate reducing agent, for example a complex metal hydride or hydrogen in the presence of a hydrogenation catalyst, reductive amination or Leuckart-Wallach reaction of an aldehyde or ketone or Gabriel reaction of an alkyl halide or alkyl tosylate. In order to prepare the cyclohexylamines, the starting materials for the particularly preferred cis-cyclohexylamino derivatives a particularly suitable method is the reductive amination of suitably substituted cyclohexanones with ammonium salts and sodium cyanoborohydride or with ammonia and hydrogen in the presence of metal catalysts such as nickel, ruthenium, rhodium or palladium, in which method the proportion of the desired cis amine is particularly high. A further method is the hydrogenation of anilines in the presence of hydrogenation catalysts.

Suitable reactions for the preparation of the starting materials for the particularly preferred cyclohexyl derivatives are, in particular:

1.) Alkenyl derivatives (n=5, U=direct bond, $R^5$=alkenyl)

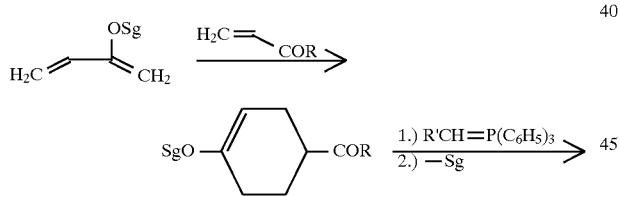

Sg=protective group

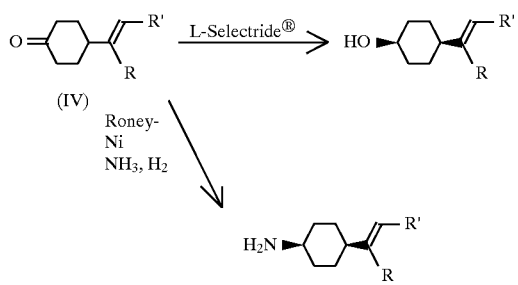

Particularly suitable protective groups Sg are trialkylsilyl groups such as the trimethylsilyl or tert-butyl dimethylsilyl group. The substituents. R and R' can be varied widely (e.g. R=H, alkyl, aryl; R'=H, alkyl, aryl, heterocyclyl, alkanoyl, etc.).

For the cycloaddition: J. Amer. Chem. Soc. 103, 6677 (1981); J. Organomet. Chem. 201, C9 (1980); J. Org. Chem. 50, 531 (1985); Org. Synth. coil. vol. VI, 445.

2.) Alkynyl derivatives (m=5, U=direct bond, $R^5$=alkynyl)

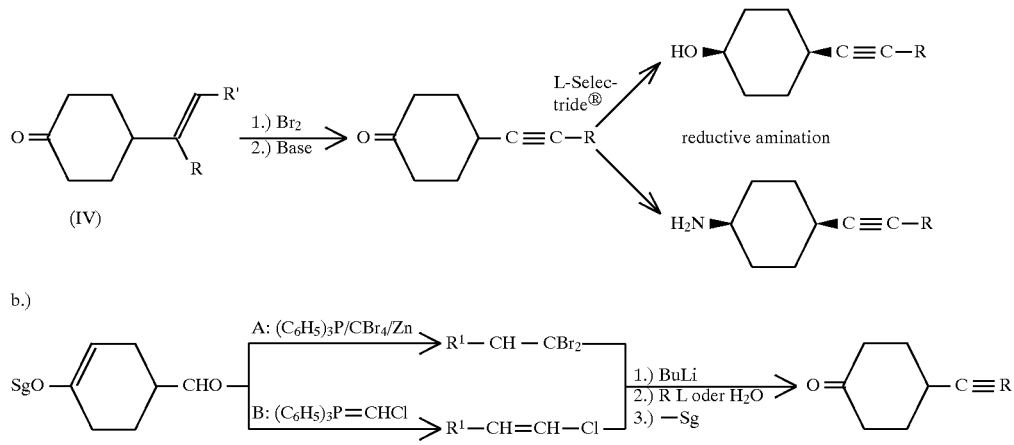

Tetrahedron Lett. 1972, 3769 R=e.g. H, alkyl, $Si(CH_3)_3$

J. Amer. Chem. Soc. 83, 1617 (1961)

Synthesis 1975, 458

3.) Haloalkyl derivatives (n=5, U=direct bond, $R^5$=haloalkyl)

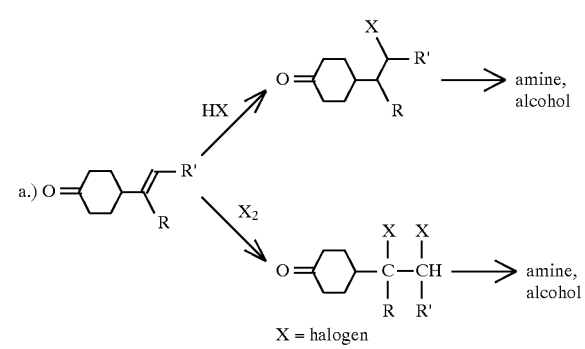

X = halogen

For the preparation of vicinal difluoro compounds for R'=aryl: J. Chem. Soc. 1994, 343

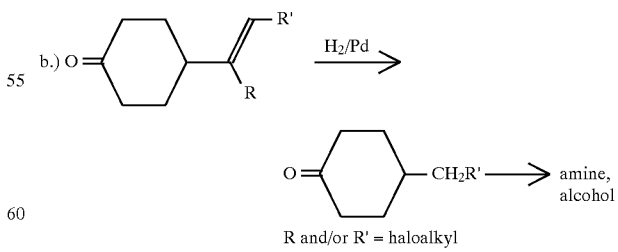

R and/or R' = haloalkyl

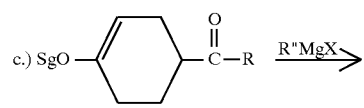

-continued

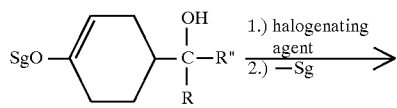

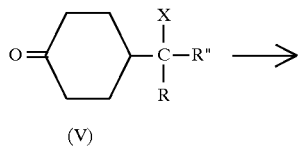

Examples of halogenating agents are DAST for X=F or SOCl$_2$ for X=Cl

If NaBH$_4$ is employed instead of R"MgX, sec-alkyl derivatives are obtained correspondingly.

The halogen derivatives of the formula V can in turn be used to prepare olefin derivatives:

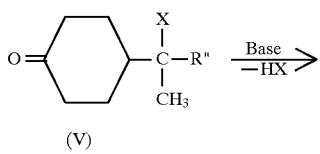

-continued

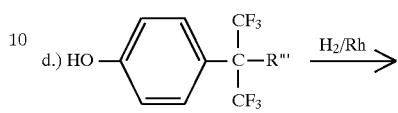

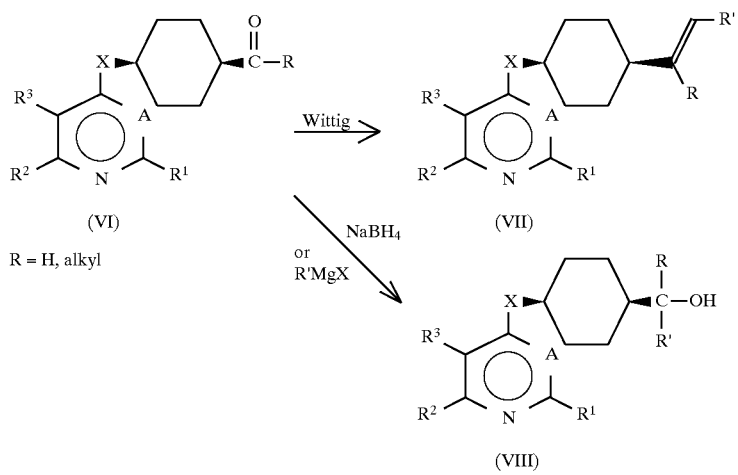

4.) Reactions with the exception of those described under 3d) can also be carried out starting from the 4-acyl-cyclohexyl derivatives of the formula VI or their follow-on products of the formula VII, in which case the end products I are obtained directly.

For example:

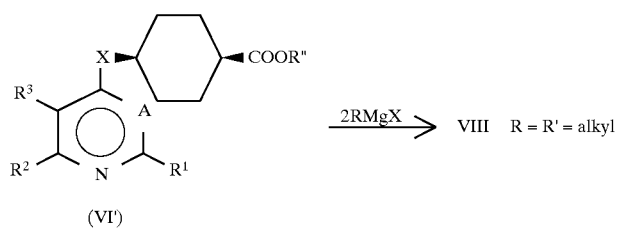

Preparation of the compounds VI: DE-A-44 17 163.

The hydroxyalkyl derivatives VIII can be reacted to give ether derivatives, by reaction with compounds R"X, in which R" is an appropriate organic radical (alkyl, activating aryl, heteroaryl) and X is a leaving group or an acidic OH group (Williamson's ether synthesis, Mitsunobu reaction)

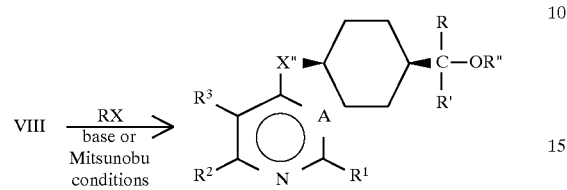

In addition, the products VIII can be converted, via the haloalkyl derivatives IX, into cyanoalkyl, nitroalkyl, thiocyanoalkyl, thioether and ether derivatives X

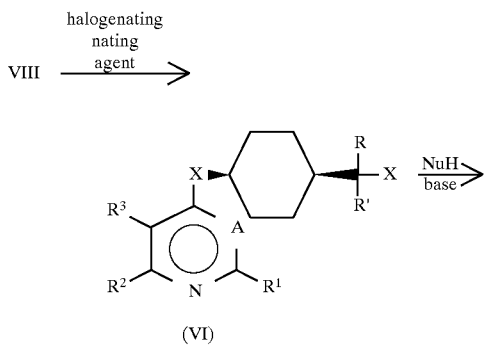

Examples of halogenating agents are SOCl$_2$, PBr$_3$, DAST.

It is also possible to obtain alkenyl compounds VII from the hydroxyalkyl derivatives VIII and the haloalkyl derivatives IX

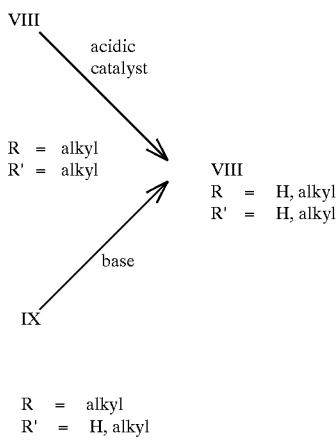

5.) The starting materials for the compounds of the formula I in which U is a direct bond and R$^5$ is a group can, if Y is carbon and R$^{10}$ is, for example, a methyl group linked to Y, be prepared as follows

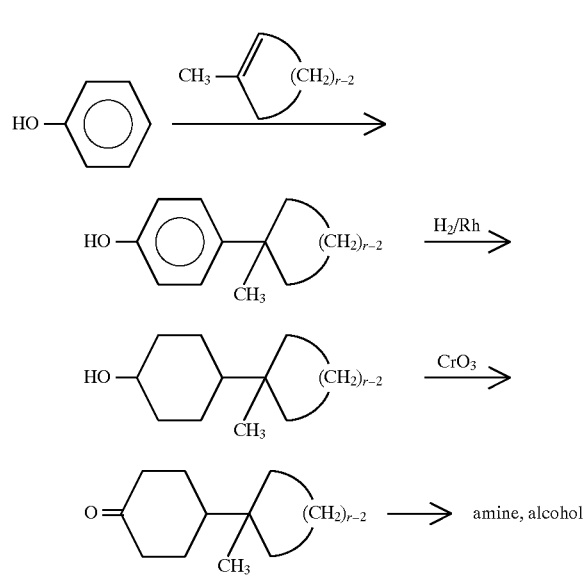

For the specific case in which r is 2 (cyclopropyl derivatives), these derivatives can be synthesized as follows:

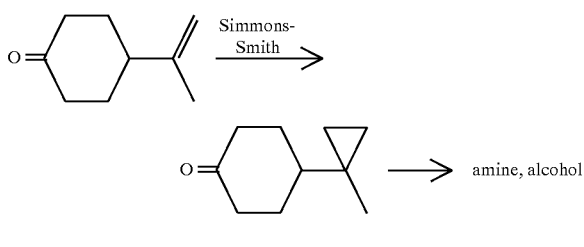

Those compounds for which Y is silicon can be synthesized as follows:

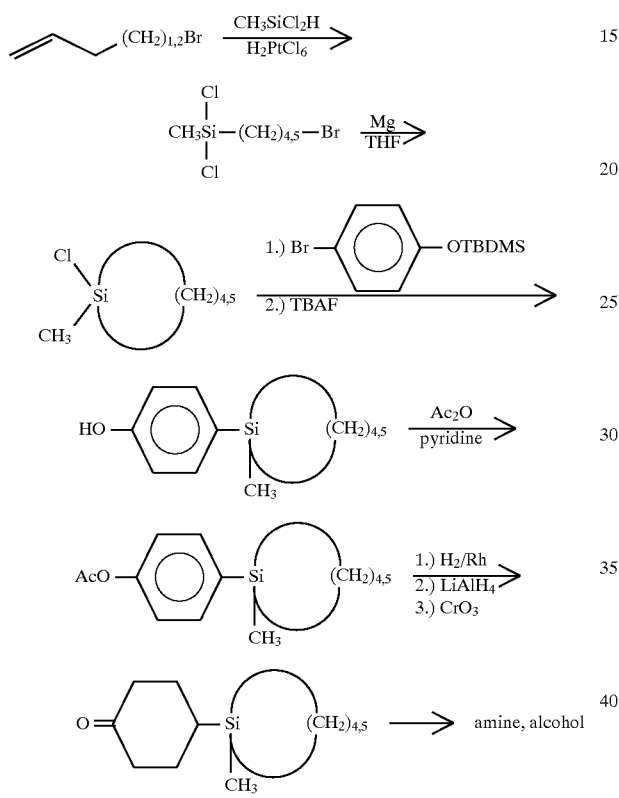

6.) Derivatives for which U is oxygen or $S(O)_m$, for example: haloalkoxy, alkylthio, alkylsulfinyl or alkylsulfonyl derivatives, cyano derivatives (U=direct bond, $R^5\uparrow CN$)

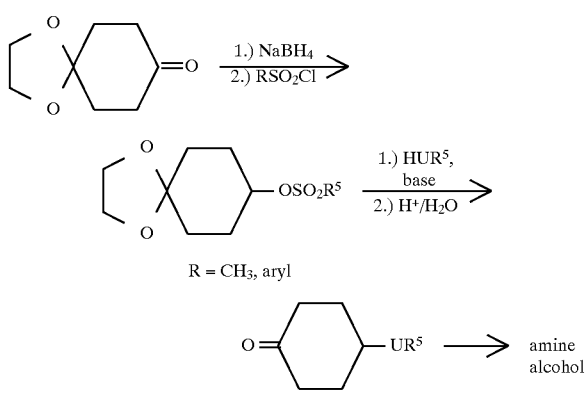

The corresponding end products can also be obtained directly by the following reaction:

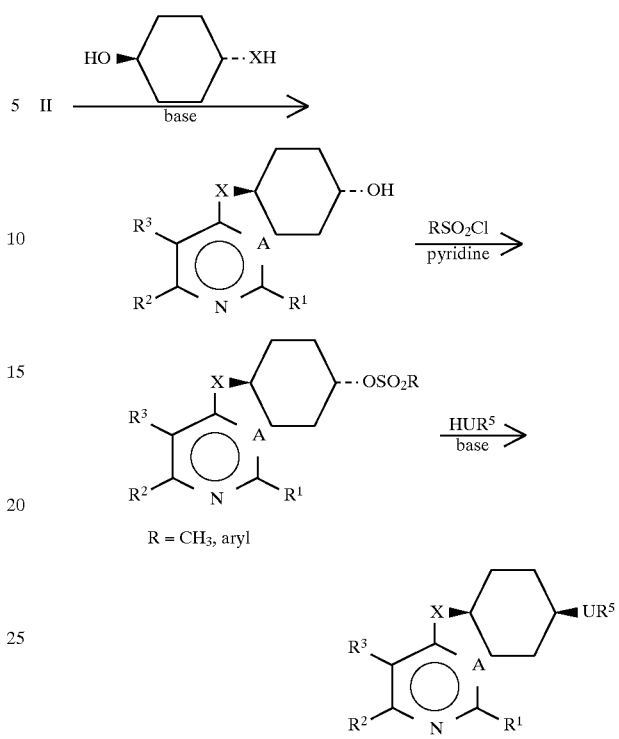

If the reactions are carried out with thiols, it is likewise possible to obtain, from the resulting thioethers (U=S) by oxidation, for example with peracids, the corresponding sulfinyl (U=SO) and sulfonyl (U=$SO_2$) derivatives. Nitro and thiocyano derivatives ($UR^5$=$NO_2$, SCN) can also be obtained by this method.

7.) ($R^6R^7R8Si$)-alkyl derivatives

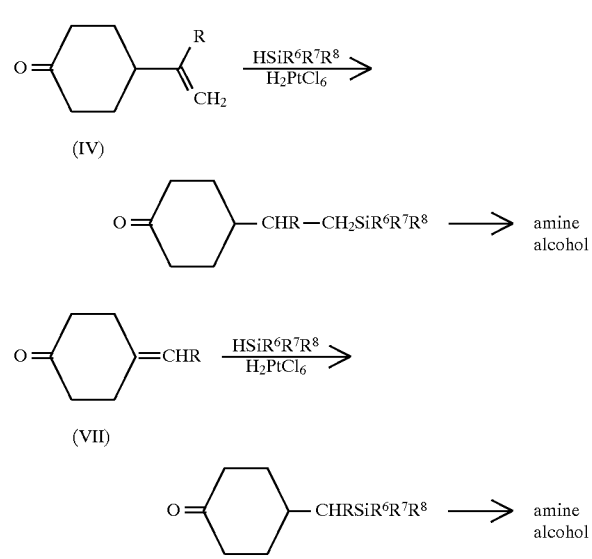

For the preparation of the exo-methylene derivatives VII: DE-A-43 31 178.

The analogous reactions on the heterocyclic derivatives of the formula VIII and IX lead directly to the end products

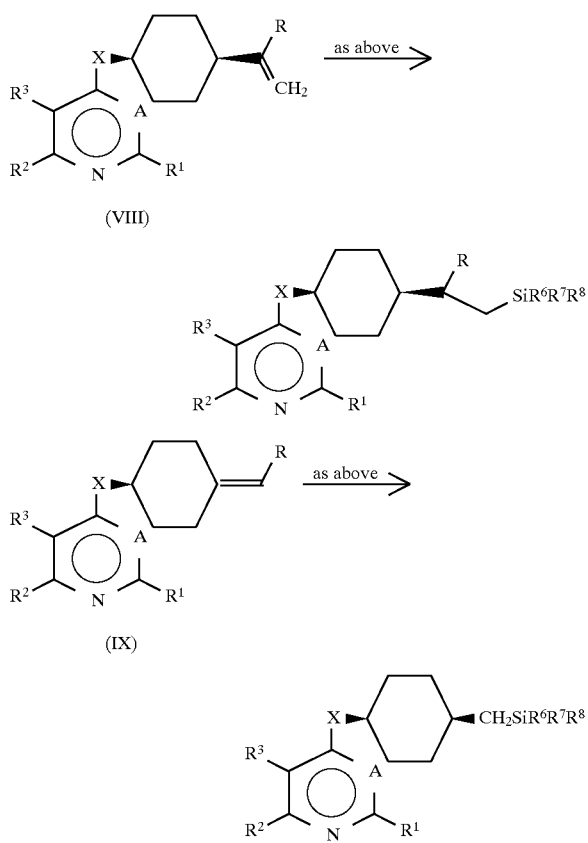

For the preparation of the exo-methylene derivatives of the formula IX: DE-A-43 31 178.

The active compounds are suitable for combating animal pests, in particular insects, arachnids, nematodes and molluscs, very particularly preferably for combating insects and arachnids, encountered in agriculture, in animal keeping, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp. and Eutetranychus spp.

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae,* *Blatella germanica, Acheta domesticus,* Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis and Fasciola.

From the class of the Gastropoda, for example, Deroceras spp., Arion spp., Lymnaea spp., Galba spp.,Succinea spp., Biomphalaria spp., Bulinus spp. and Oncomelania spp.

From the class of the Bivalva, for example, Dreissena spp.

The plant-parasitic nematodes which can be controlled according to the invention include, for example, the root-parasitic soil-dwelling nematodes, such as, for example, those from the genera Meloidogyne (root-knot eel worms, such as *Meloidogyne incognita, Meloidogyne hapla* and *Meloidogyne javanica*), Heterodera and Globodera (cyst nematodes, such as *Globodera rostochiensis, Globodera pallida, Heterodera trifolii*) and of the genera Radopholus, such as *Radopholus similis,* Pratylenchus, such as *Pratylenchus neglectus, Pratylenchus penetrans* and *Pratylenchus curvitatus;*

Tylenchulus, such as *Tylenchulus semipenetrans,* Tylenchorhynchus, such as *Tylenchorhynchus dubius* and *Tylenchorhynchus claytoni,* Rotylenchus, such as *Rotylenchus robustus,* Heliocotylenchus, such as *Haliocotylenchus multicinctus,* Belonoaimus, such as *Belonoalmus longicaudatus,* Longidorus, such as *Longidorus elongatus,* Trichodorus, such as *Trichodorus primitivus,* and Xiphinema, such as *Xiphinema index.*

Furthermore, the compounds according to the invention can be used for controlling the nematode genera Ditylenchus (stem parasites, such as *Ditylenchus dipsaci* and *Ditylenchus destructor*), Aphelenchoides (foliar nematodes, such as *Aphelenchoides ritzemabosi*) and Anguina (seed-gall nematodes, such as *Anguina tritici*).

The invention also relates to compositions, especially insecticidal and acaricidal compositions, which comprise the compounds of the formula I in addition to suitable formulation auxiliaries.

The compositions according to the invention generally contain the active compounds of the formula I in an amount of 1 to 95% by weight.

They can be formulated in various ways, as predetermined by the biological and/or chemicophysical parameters. The following possibilities are therefore suitable for formulation:

Wettable powders (WP), emulsifiable concentrates (EC), aqueous solutions (SL), emulsions, sprayable solutions, dispersions on an oil or water base (SC), suspoemulsions (SE), dusting agents (DP), seed-dressing agents, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical technology], Volume 7, C. Hauser Verlag, Munich, 4th Edition 1986; van Falkenberg, "Pesticides Formulations", Marcel Dekker N.Y. 2nd Ed. 1972–73; K. Martens, "Spray Drying Handbook", 3rd Ed. 1979, G. Goodwin Ltd., London.

The formulation auxiliaries required, such as inert materials, surfactants, solvents and other additives, are likewise known and are described, for example, in:

Watkins, "Handbook of Insecticide Dust Diluents and Carriers", 2nd Ed., Darland Books, Caldwell N.J.; H. v. Olphen, "Introduction of Clay Colloid Chemistry", 2nd Ed., J. Wiley & Sons, N.Y.; Marschen, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical technology], Vol. 7, C. Hauser Verlag, Munich, 4th Edition, 1986.

On the basis of these formulations, it is also possible to produce combinations with other pesticidally active substances, fertilizers and/or growth regulators, for example in the form of a readymix or as a tank mix. Wettable powders are preparations, uniformly dispersible in water, which contain, besides the active compound and in addition to a diluent or inert material, wetting agents, for example polyoxethylated alkylphenols, polyoxethylated fatty alcohols, alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active compound in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as Ca dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talcum, natural clays such as kaolin, bentonite, pyrophillite or diatomaceous earth. Granules can be prepared either by atomizing the active compound onto adsorptive, granulated inert material or by applying active compound concentrates onto the surface of carrier materials such as sand or kaolinites, or of granulated inert material by means of adhesives, for example polyvinyl alcohol or sodium polyacrylate, or alternatively mineral oils. Suitable active compounds can also be prepared in the fashion conventional for the preparation of fertilizer granules, if desired as a mixture with fertilizers.

In wettable powders, the concentration of active substance is for example about 10 to 90% by weight, with the remainder to 100% by weight being composed of conventional formulation components. In the case of emulsifiable concentrates, the concentration of active substance can be from about 5 to 80% by weight. Formulations in the form of dusts usually contain 5 to 20% by weight of active substance, while sprayable solutions contain about 2 to 20% by weight. In the case of granules, the content of active substance depends partly on whether the active compound is liquid or solid and on which granulation auxiliaries, fillers, etc. are used.

In addition, the active substance formulations mentioned include, if desired, the adhesives, wetting agents, dispersing agents, emulsifiers, penetrants, solvents, fillers or carriers which are conventional in each case.

For use, the concentrates—present in commercially available form—are diluted, if desired, in a customary manner, for example using water in the case of wettable powders, emulsifiable concentrates, dispersions and, in some cases, in the case of microgranules as well. Preparations in the form of dusts and granulated preparations, and sprayable solutions as well, are usually not diluted further with other inert substances before use.

The application rate required varies with the external conditions, such as temperature and humidity, inter alia. It can vary within wide limits, for example between 0.0005 and 10.0 kg/ha or more of active substance; preferably, however, it is between 0.001 and 5 kg/ha.

The active compounds according to the invention may be present in their commercially available formulations, and in the application forms prepared from these formulations, in mixtures with other active compounds, such as insecticides, attractants, sterilizing agents, acaricides, nematicides, fungicides, growth regulators or herbicides.

The pesticides include, for example, phosphates, carbamates, carboxylates, formamidines, tin compounds and substances produced by microorganisms, inter alia.

Preferred co-components are 1. from the group comprising the phosphorus compounds acephate, azamethiphos, azinphos-ethyl, azinphosmethyl, bromophos, bromophos-ethyl, chlorfenvinphos, chlormephos, chlorpyrifos, chlorpyriphosmethyl, demeton, demeton-S-methyl, demeton-S-methylsulfone, dialifos, diazinon, dichlorvos, dicrotophos, 0,0-1,2,2,2-tetrachloroethyl phosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemetonmethyl, parathion, parathionmethyl, phenthoate phorate, phosalone, phosfolan, phosmet, phosphamidon, phoxim, pirimiphos, pirimophos-ethyl, pirimiphos-methyl, profenofos, propaphos, proetamphos, prothiofos, pyraclofos, pyridapenthion, quinalphos, sulprofos, temephos, terbufos, tetraclorvinphos, thiometon, triazophos, trichlorphon, vamidothion;

2. from the group comprising the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5, 11 -dithia-9-dodecenoate (OK 135), 1 -methylthio(ethylideneamino) N-methyl-N-(morpholinothio)carbamate (UC 51717);

3. from the group comprising the carboxylates allethrin, alphametrin, 5-benzyl-3-furylmethyl (E)-(1R) cis-2,2-dimethyl-3-(2-oxothiolan-3-ylidenemethyl) cyclopropanecarboxylate, bioallethrin, bioallethrin ((S) cyclopentyl isomer), bioresmethrin, biphenate, (RS)-1-cyano-1-(6-phenoxy-2-pyridyl)methyl (1 RS)-trans-3-(4-tertbutylphenyl)-2,2-dimethylcyclo propanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomers), permethrin, phenothrin ((R) isomers), d-pralethrin, pyrethrins (natural products), resmethrin, tefluthrin, tetramethrin, tralomethrin;

4. from the group comprising the amidines amitraz, chlordimeform;

5. from the group comprising the tin compounds cyhexatin, fenbutatin oxide;

6. others abamectin, *Bacillus thuringiensis,* bensultap, binapacryl, bromopropylate, buprofezin, camphechlor, cartap, chlorobenzilate, chlorfluazuron, 2-(4-chlorophenyl)-4,5-diphenylthiophene (UBI-T 930), clofentezine, 2-naphthylmethyl cyclopropanecarboxy-late (Ro 12-0470), cyromazin, DDT, dicofol, N-(N-(3, 5-dichloro-4-(1,1,2,2-tetrafluoroethoxy)phenyl)amino) carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl) (3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MT1 800), granulosis and nuclear polyhedrosis viruses fenthiocarb, flubenzimine, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron and imidacloprid.

The active compound content of the use forms prepared from the commercially available formulations can be from 0.00000001 to 95% by weight of active compound, preferably between 0.00001 and 1% by weight.

Application is effected in a conventional fashion, matched to the use forms.

The active compounds according to the invention are also suitable for combating ecto- and endoparasites in the area of veterinary medicine or in the area of animal keeping.

The active compounds according to the invention are applied here in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The novel compounds, according to the invention, of the formula I can accordingly also be employed particularly advantageously in the keeping of livestock (for example cattle, sheep, pigs and poultry such as chickens, geese, etc.). In a preferred embodiment of the invention, the novel compounds, if appropriate in suitable formulations (cf. above) and if appropriate with the drinking water or feed, are administered orally to the animals; Since excretion in the droppings occurs in an effective fashion, the development of insects in the animal droppings can be prevented very simply in this fashion. The dosages and formulations suitable in each case are particularly dependent on the type and stage of development of the productive animals and also on the degree of infestation of the insects, and can easily be determined and fixed by conventional methods. In the case of cattle, the novel compounds can be employed, for example, in dosages of 0.01 to 1 mg/kg of body weight.

The compounds of the formula I according to the invention are also distinguished by an outstanding fungicidal action. Fungal pathogens which have already penetrated the plant tissue can successfully be controlled curatively. This is particularly important and advantageous in the case of those fungal diseases which can no longer be controlled effectively with the otherwise conventional fungicides once infection has taken place. The spectrum of action of the claimed compounds embraces a variety of economically important phytopathogenic fungi such as, for example, *Plasmopara viticola, Phytophthora infestans, Erysiphe graminis, Piricularia oryzae, Pyrenophora teres, Leptosphaerea nodorum* and *Pellicularia sasakii* and *Puccinia recondita.*

In addition, the compounds according to the invention are also suitable for use in industrial areas, for example as wood preservatives, as preservatives in paints, in cooling lubricants for metalworking, or as a preservative in drilling and cutting oils.

The active substances according to the invention can be employed in their commercially available formulations, either alone or in combination with other fungicides known from the literature.

Examples of fungicides known from the literature which can be combined according to the invention with the compounds of the formula I are the following products:

aldimorph, andoprim, anilizine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezin, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidine, fenpropimorph, fentin acetate, fentin hydroxide, ferimzone (TF 164), fluazinam, fluobenzimine, fluquinconazole, fluorimide, flusilazole, flutolanil, flutriafol, folpet, fosetylaluminium, fuberidazole, fulsulfamide (MT-F 651), furalaxyl, furconazol, furmecyclox, guazatine, hexaconazole, ICI A5504, imazalil, imibenconazole, iprobenfos, iprodione, isoprothiolane, KNF 317, copper compounds such as Cu oxychloride, oxine-Cu, Cu oxide, mancozeb, maneb, mepanipyrim (KIF 3535), metconazol, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilone, rabenzazole, RH 7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15 alcohol ether sulfonate, sodium cetostearyl phosphate ester, dioctyl sodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The abovementioned co-components are known active compounds, many of which are described in Ch. R. Worthing, S. B. Walker, The Pesticide Manual, 7th Edition (1983), British Crop Protection Council. The active substance content of the use forms prepared from the commercially available formulations can be varied within wide limits; the concentration of active compound in the use forms can be from 0.0001 to 95% by weight of active compound and is preferably between 0.0001 and 1% by weight. The use forms are employed in a customary manner adapted to suit them.

The following examples serve to illustrate the invention without limiting it thereto.

A. Formulation Examples a) A dusting agent is obtained by mixing 10 parts by weight of active compound and 90 parts by weight of talcum as inert material and comminuting in a hammer mill.

b) A wettable powder which is easily dispersible in water is obtained by mixing 25 parts by weight of active compound, 65 parts by weight of kaolin-containing quartz as inert material, 10 parts by weight of potassium ligninsulfonate and 1 part by weight of sodium oleoylmethyltaurinate as wetting and dispersing agent, and grinding in a pin disk mill.

c) A dispersion concentrate which is easily dispersible in water is prepared by mixing 40 parts by weight of active compound with 7 parts by weight of a sulfosuccinic acid monoester, 2 parts by weight of a sodium ligninsulfonate and 51 parts by weight of water and grinding in a ball mill to a fineness of below 5 microns.

d) An emulsifiable concentrate can be prepared from 15 parts by weight of active compound, 75 parts by weight of cyclohexane as solvent and 10 parts by weight of oxethylated nonylphenol (10 EO) as emulsifier.

e) Granules can be prepared from 2 to 15 parts by weight of active compound and an inert granule carrier material such as attapulgite, granulated pumice and/or quartz sand. Advantageously, a suspension of the wettable powder from Example b) is used which has a solids content of 30%, and this suspension is sprayed onto the surface of attapulgite granules, dried and intimately mixed. In this case, the proportion by weight of the wettable powder is about 5% and that of the inert carrier material is about 95% of the finished granules.

B. Biological examples

Insecticidal and acaricidal action

EXAMPLE 1

Action on the Brown Planthopper

Young rice plants (Oryza sativa) were immersed in aqueous dilutions of a wettable powder concentrate at a concentration of 250 ppm (based on active compound) and, after the treatment mixture had run off, were populated with L4 larvae of the brown planthopper *Nilaparvata lugens*.

After the test animals had been introduced into a test cage, they were observed for 3 days at 28° C. and high atmospheric humidity, and their mortality was determined.

At 250 ppm, the compounds according to Example 1, 2, 5, 6, 12, 14, 16, 18, 19, 20, 21, 22, 24, 25, 27, 28, 29, 30, 31, 32, 33, 39, 40, 41, 42, 44, 49, 50, 51, 53, 59 and 60 resulted in a 100% mortality of the test animals.

EXAMPLE 2

Action on *Diabrotica Undecimpunctata*

Larvae (L3) of the Southern Corn Rootworm (*Diabrotica undecimpunctata*) were placed on filter paper disks which had been soaked in 1 ml of a dilution of a wettable powder in acetone at a concentration of 250 ppm based on active compound. After the acetone had evaporated, the dishes were sealed and stored for 3 days at 28° C., and the mortality of the larvae was then determined.

The compounds according to Example 1, 2, 5, 6, 12, 14, 16, 20, 24, 25, 28, 34, 35, 36, 37, 39, 40, 41, 42, 49, 50, 52, 53, 56, 59, 60, 61, 62, 65, 66 and 67 showed a mortality of 100%.

EXAMPLE 3

Action on the Eggs of the Large Milkweed Bug

Filter paper disks with two-day-old eggs of the large milkweed bug (*Oncopeltus fasciatus*) placed thereon were treated with 1 ml each of an aqueous preparation which contained 250 ppm of the respective active compound. After the coating had dried on, the filter paper disks were stored at room temperature and maximum atmospheric humidity in Petri dishes. The ovicidal action was determined after 7 days. 100% ovicidal action (mortality of the eggs) was found with Examples 1, 2, 3, 5, 6, 12, 14, 16, 17, 18, 19, 22, 24, 25, 26, 27, 33, 34, 39, 41, 42, 52, 57 and 67.

EXAMPLE 4

Action on the Black Bean Aphid

Field bean plants (*Vicia faba*) heavily infested with black bean aphids (*Aphis fabae,* complete population) were sprayed up to the beginning of runoff with an aqueous preparation which contained 250 ppm of the respective active compound. After cultivation of the plants under glass for 3 days, the mortality of the aphids (complete population) was checked. 100% mortality was found with Examples 1, 5, 6, 14, 16, 18, 19, 22, 23, 24, 25, 26, 28, 29, 31, 40, 41, 42, 44, 45, 46, 48, 49, 50, 52, 53, 54, 56, 59, 70, 71 and 72.

EXAMPLE 5

Action on the Red Spider Mite

Bean plants (Phaseolus vulgaris ssp. *vulgaris cv. nanus*) heavily infested with red spider mites (*Tetranychus urticae,* complete population) were sprayed up to the beginning of runoff with an aqueous preparation which contained 250 ppm of the respective active substance. After cultivation of the plants under glass for 7 days, the mortality of the spider mites (complete population) was checked. 100% mortality was found with Examples 2, 6, 14, 18, 19, 22, 23, 25, 26, 27, 28, 29, 30, 31, 33, 34, 35, 36, 37, 38, 40, 41, 42, 43, 44, 45, 46, 47, 48, 49, 50, 51, 52, 53, 54, 55, 56, 57, 59, 60, 62, 63, 65, 66, 67, 68, 70, 71, 72, 73 and 74.

EXAMPLE 6

Action on the Fruit Tree Red Spider Mite

Apple plants (*Malus domestica*) heavily infested with fruit tree spider mites (*Panonychus ulmi,* complete population) were sprayed up to the beginning of runoff with an aqueous preparation which contained 250 ppm of the respective active compound. After cultivation of the plants under glass for 9 days, the mortality of the fruit tree red spider mites (complete population) was checked. 100% mortality was found with Examples 1, 6, 22, 23, 24, 25, 26, 27, 28, 29, 30, 32, 33, 34, 35, 36, 37, 39, 40, 41, 49, 50, 51, 52, 53, 54, 59, 60, 61, 62, 63, 65, 66 and 67.

EXAMPLE 7

Action on the Citrus Mealybug

Bean plants (Phaseolus vulgaris ssp. *vulgaris cv. nanus*) heavily infested with citrus mealybug (*Planococcus citri,* larvae of the 2nd development stage) were sprayed up to the beginning of runoff with an aqueous preparation which contained 250 ppm of the respective active compound. After cultivation of the plants under glass for 7 days, the mortality of the citrus mealybugs (complete population) was checked. 100% mortality was found with Examples 1, 5, 6, 24 and 25.

EXAMPLE 8

Action on the Housefly

The base and lid of a Petri dish are coated on the inside with 3 ml each of an aqueous dilution of a wettable powder concentrate containing 250 ppm of the respective active compound. After the spray coating had dried on, houseflies (*Musca domestica*) aged 24 hours were placed in the Petri dishes, which were sealed with the coated lid. After 3 hours at 20° C., the mortality of the flies was checked. 100% destruction was obtained with compounds 1, 3, 5, 6, 12, 14, 16, 17, 18, 19, 23, 24, 25, 26, 27, 28, 29, 30, 31, 32, 35, 36, 39, 40, 41, 42, 44, 45, 46, 49, 52, 53, 54, 55, 60, 61, 62 and 64.

EXAMPLE 9

Ovicidal Action (*Manduca sexta*)

The inside of the bottom of Petri dishes was covered with Japan filter paper, and 20 eggs, 1 day old, of *Manduca sexta* were placed on the paper in each dish. Approximately 1 ml of a synthetic insect feed diet was placed in the center of the Petri dish, and the inside of the bottom complete with eggs and feed diet was sprayed with an aqueous wettable powder suspension of the test products corresponding to 600 I/ha. The Petri dishes were then sealed and stored at room temperature for 5 days, after which the mortality of the eggs was determined. 100% action was achieved by the compounds of Examples 1, 2, 5, 6, 12, 14, 16, 17, 18, 22, 23, 24, 25, 27, 30, 33, 34, 37, 39, 41, 42, 49, 51, 52, 57 and 65.

EXAMPLE 10

Larvae (L4) of the cockroach *Blaberus craniifer* were injected with active compounds dissolved in methanol. After application of the compounds according to Examples 1 and 6 ($2 \times 10^{-4}$ g a.i./animal), a 100% mortality was found after 48 hours.

EXAMPLE 11

Larvae (L4) of the tobacco hornworm *Manduca sexta* were injected with active compounds dissolved in acetone. After application of the compound according to Examples 1 and 5 ($2 \times 10^{-4}$ g a.i./animal), a 100% mortality was found after 48 hours.

Use as an antiparasitic

EXAMPLE 12

In vitro Test on Tropical Cattle Ticks (*Boophilus microplus*)

The following experimental set-up demonstrated the activity of the compounds according to the invention against ticks:

To prepare a suitable preparation of active compound, the active compounds were dissolved in a mixture composed of dimethylformamide (85 g), nonylphenol polyglycol ether (3 g) and ethoxylated castor oil (7 g) to give a 10% (W/V) solution, and the resulting emulsion concentrates were diluted with water to a test concentration of 500 ppm.

Batches of 10 satiated females of the tropical tick *Boophilus microplus* were immersed for five minutes in these dilutions of active compound. The ticks were subsequently dried on filter paper, and their backs were then attached to an adhesive film for the purpose of oviposition. The ticks were kept in an incubation cabinet at 28° C. and at atmospheric humidity of 90%.

As a control, female ticks were immersed in water only. The activity was assessed two weeks after the treatment, on the basis of inhibition of oviposition.

In this test, the compound of Examples 6, 12, 14, 22, 24, 25, 28, 29, 30, 31, 32, 33, 34, 35, 36, 38, 40, 50, 51, 54, 55, 56, 63, 65, 66, 69 brought about in each case a 100% inhibition of oviposition in an active compound concentration of 500 ppm.

Use as a fungicide

The activity of the preparations according to the invention was assessed in accordance with a scale of 0 to 4 in which 0 0–24% suppression of infestation
1 25–49% suppression of infestation
2 50–74% suppression of infestation
3 75–97% suppression of infestation
4 98–100% suppression of infestation.

EXAMPLE 13

Barley plants of the variety "Maris Otter" at the 2-leaf stage were sprayed until dripping wet with a solution of the compounds according to the invention in a mixture of 40% acetone and 60% water. 24 hours later, the plants were innoculated with conidia of powdery mildew of barley (*Erysiphe graminis* f. sp. hordei) and kept in a climatically controlled chamber at 20° C. with a relative atmospheric humidity of from 75 to 80%. 7 days after the treatment, the plants were investigated for infestation with powdery mildew of barley. The following compounds were assessed at 3 or 4 at 50 mg of active compound/I of spray liquor:
Compounds according to Example Nos. 28, 29, 30 and 62.

EXAMPLE 14

Tomato plants of the variety "First in the Field" at the 3–4 leaf stage were sprayed until dripping wet with a solution of the compounds according to the invention in a mixture of 40% acetone and 60% water. 24 hours later, the plants were innoculated with a spore suspension of *Phytophthora infestans* (20,000 spores/ml) and kept in a climatically controlled chamber at 15° C., first for 2 days at 99% relative atmospheric humidity, then for 4 days at 75 to 80% relative atmospheric humidity. 6 days after treatment, the plants were investigated for infestation with *Phytophthora infestans*.

The following compounds received an assessment of 3 or 4 at 50 mg of active substance/I of spray liquor:
Compounds according to Example Nos. 16, 24, 25, 27, 28, 29, 30, 32 and 63.

EXAMPLE 15

Approximately 6-week-old seedlings of the vine variety "Grüner Veltliner" were sprayed until dripping wet with a solution of the compounds according to the invention in a mixture of 40% acetone and 60% water. 24 hours later, the plants were inoculated by spraying with a zoospore suspension (100,000/ml) of *Plasmopara viticola* and were kept in a climatically controlled chamber at 70° C. with a relative atmospheric humidity of about 99%. 14 days after treatment, the plants were investigated for their infestation with *Plasmopara viticola*.

The following compounds were given an assessment of 3 or 4 at 50 mg of active substance/I of spray liquor:
Compounds according to Example Nos. 5, 22, 28, 30, 62, 63 and 64.

EXAMPLE 16

Rice plants of the variety "Nihonbare" at the 1.5 leaf stage were sprayed until dripping wet with a solution of the compounds according to the invention in a mixture of 40% acetone and 60% water. At the same time, application by watering was carried out with a solution of the substances in a mixture of 5% acetone and 95% water. 24 hours later, the plants were innoculated by spraying with a pycnospore suspension ($10^6$/ml) of *Pyricularia oryzae*. The plants were kept for 2 days in a darkened climatically controlled chamber at 26° C. with a relative atmospheric humidity of 99%, and then moved to a lit climatically controlled chamber at about 18° C. and a relative atmospheric humidity of 75 to 80%. 7 to 9 days after innoculation, the plants were investigated for their infestation with *Pyricularia oryzae*.

The following substances received an assessment of 3 or 4 at 50 mg of active substance/I of spray liquor:
Compounds according to Example Nos. 1, 5, 25, 28 and 80.

C. Preparation Examples

EXAMPLE 1

5-Chloro-6-ethyl-4-[cis-4-(2-hydroxy-2-propyl) cyclohexylamino]pyrimidine 10.4 g (33 mmol) of ethyl cis-4-(5-chloro-6-ethylpyrimidin-4-ylamino)cyclohexanecarboxylate (preparation: DE-A-44 17 163) were placed in 100 ml of dry tetrahydrofuran, and 100 ml (0.1 mol) of 1M methylmagnesium bromide solution were added dropwise at 20° C. under a nitrogen atmosphere. The mixture was subsequently stirred at room temperature for 2 hours and at 50° C. for 2 hours, poured into saturated ammonium chloride solution and diluted with 200 ml of toluene. The organic phase was dried and concentrated. For purification, it was chromatographed on silica gel with ethyl acetate as eluent. 6.0 g (61% of theory) were obtained of a colorless oil which solidified on standing. m.p.: 75° to 76° C.

EXAMPLE 2

5-Chloro-6-ethyl-4-[cis-4-(2-hydroxy-1,1,1-trifluoro-2-propyl)cyclohexylamino]pyrimidine 1.3 g (7.2 mmol) of 4,5-dichloro-6-ethylpyrimidine, 2.7 g (7.2 mmol) of 1-amino-4-(2-hydroxy-1,1,1-trifluoro-2-propyl)cyclohexane and 1.5 g (17.1 mmol) of potassium carbonate were stirred in 10 ml of dimethylformamide at from 80° to 90° C. for 6 hours. The solvent was stripped off and the residue was taken up in water/diethyl ether, and the organic phase was washed with water, dried and concentrated. For purification it was chromatographed on silica gel (ethyl acetate). 1.0 g of product was obtained as colorless crystals. m.p.: 119to 121° C.

Preparation of the precursors:

1-Amino-4-(2-hydroxy-1,1,1-trifluoro-2-propyl) cyclohexane 11.1 g (53 mmol) of 4-(2-hydroxy-1,1,1-trifluoro-2-propyl)cyclohexanone were subjected to reductive amination in 150 ml of ammonia-saturated methanol in the presence of 2.3 g of rhodium (5% on charcoal) with 50 bar of hydrogen. 9.0 g (80.1% of theory) were obtained of a colorless oil which was reacted without further purification.

4-(2-Hydroxy-1,1,1-trifluoro-2-propyl) cyclohexanone 18.8 g (0.089 mol) of 4-(2-hydroxy-1,1,1-trifluoro-2-propyl)cyclohexanol were placed in a mixture of 350 ml of acetone and 20 ml of water, and 50 ml of Jones' reagent were added dropwise at from 10° to 15° C. The mixture was subsequently stirred at room temperature for 1 hour, 10 ml of isopropanol were added, and after a further 30 minutes the mixture was neutralized with 40 g of sodium bicarbonate. It was then filtered, the filtrate was concentrated and the residue was taken up with water/diethyl ether. After drying and concentration of the organic phase, 11.1 g (59.6% of theory) remained of a colorless product.

4-(2-Hydroxy-1,1,1 -trifluoro-2-propyl)cyclohexanol 18.9 g (0.092 mol) of 4-(2-hydroxy-1,1,1-trifluoro-2-propyl)phenol were hydrogenated in a mixture of 200 ml of isopropanol and 6 ml of concentrated hydrochloric acid in the presence of 2.3 g of rhodium (5% on charcoal) at 150 bar and 50° C. After filtration to remove the catalyst and concentration, 18.8 g (96.6% of theory) remained of a colorless product.

4-(2-Hydroxy-1,1,1-trifluoro-2-propyl)phenol 31.3 g (0.106 mol) of 4-(2-hydroxy-1,1,1-trifluoro-2-propyl)phenol benzyl ether were hydrogenated in 380 ml of glacial acetic acid in the presence of 6.3 g of palladium (5% on charcoal) at 50° C. After filtration to remove the catalyst and concentration, 18.9 g (87% of theory) remained of a colorless product.

4-(2-Hydroxy-1,1,1 -trifluoro-2-propyl)phenol benzyl ether

A solution of 30.0 g (0.107 mol) of 4-(trifluoroacetyl) phenyl benzyl ether in 50 ml of diethyl ether was added dropwise at 0° C. to a solution of 12.0 g (0.161 mol) of methylmagnesium chloride in 150 ml of diethyl ether. After 2 hours at reflux, the mixture was poured into saturated ammonium chloride solution. 31.3 g (99% of theory) were obtained of colorless product.

4-Trifluoroacetylphenol benzyl ether

A solution of 91.2 ml (0.23 mol) of 2.5M n-butyllithium solution was added dropwise at −40° C. to a solution of 50.0 g (0.19 mol) of 4-bromophenol benzyl ether in 250 ml of tetrahydrofuran. The mixture was subsequently stirred for a short time at −40° C., then cooled to −78° C., and 34 g (0.27 mol) of methyl trifluoroacetate were added dropwise. The mixture was allowed to come to room temperature and then stirred at 0° C. for 3 hours. For working up, 120 ml of dilute hydrochloric acid were added dropwise, the mixture was diluted with toluene, and the organic phase was separated off, washed with water, dried and concentrated. A brown solid was obtained which was recrystallized from petroleum ether/ethyl acetate 10:1.
Yield: 30.1 g (56.5% of theory) of a colorless solid.

EXAMPLE 3

5-Chloro-6-ethyl-4-(cis-4-hydroxymethylcyclohexylamino)pyrimidine

A solution of 12.47 g (0.040 mol) of ethyl cis-4-(5-chloro-6-ethylpyrimidin-4-ylamino)-cyclohexanecarboxylate (preparation: DE-A-44 17 163) in 25 ml of dry tetrahydrofuran was added dropwise at from 20° to 30° C. to a suspension of 1.52 g (0.04 mol) of lithium aluminum hydride in 150 ml of dry tetrahydrofuran. The mixture was subsequently stirred at 50° C. for 1 hour and cooled to room temperature, and 10 ml of water were carefully added dropwise. After removal of inorganic material by filtration with suction, the organic phase was dried and concentrated. For purification, the crude product was chromatographed on silica gel (using ethyl acetate as eluent). 5.2 g (48.2% of theory) were obtained of a yellow oil which solidified on standing. m.p.: 71° to 72° C.

the following compound was prepared analogously:

EXAMPLE 4

4-(cis-4-Hydroxymethylcyclohexylamino) quinazoline

Colorless crystals. m.p.: 60° to 62° C.

EXAMPLE 5

5-Chloro-6-ethyl-4-[cis-4-(isopropenyl) cyclohexylamino]pyrimidine 1.8 g (11 mmol) of diethylaminosulfur trifluoride (DAST) were added to 3.0 g (10 mmol) of the alcohol from Example 1 in 50 ml of dichloromethane at −50° C., and the mixture was stirred at room temperature for 1 hour. It was poured into water and the organic phase was washed with aqueous sodium hydrogen carbonate solution, dried and concentrated. The crude product was chromatographed on silica gel with petroleum ether/ethyl acetate 7:3 to give, first of all, 0.8 g (28.6% of theory) of the product indicated above as a colorless oil, and then 1.5 g (50.5% of theory) of the fluorination product described in Example 6, as a colorless oil (see Example 6).

EXAMPLE 6

5-Chloro-6-ethyl-4-[cis-( 1-fluoro- 1-methylethyl) cyclohexylamino]pyrimidine

EXAMPLE 7

5-Chloro-6-ethyl-4-[cis-4-(isopropenyl) cyclohexylamino]pyrimidine (alternative synthesis)

1.6 g (0.009 mol) of 4,5-dichloro-6-ethylpyrimidine and 1.2 g (0.009 mol) of 4-isopropenylcyclohexylamine were stirred with 1.8 g (0.013 mol) of $K_2CO_3$ in 10 ml of DMF at 80° C. for 6 hours. After cooling to room temperature, the mixture was placed in water and extracted with ether. The organic phase was washed with water, dried and filtered, and the filtrate was chromatographed on silica gel with petroleum ether/ethyl acetate 7:3 in order to separate the cis/trans isomers.

The cis-cyclohexylamino derivative is eluted first (1.4 g, yellow oil) followed by the trans-cyclohexylamino derivative (0.6 g, yellow oil).

Preparation of the precursors for Example 7

4-lsopropenylcyclohexylamine 6.7 g (0.048 mol) of 4-isopropenylcyclohexanone were hydrogenated in 40 ml of ammonia-saturated methanol in the presence of 0.5 g of Raney nickel at 50° C. and 50 bar. The catalyst was filtered off and then the mixture was concentrated. 6.3 g of a colorless liquid were obtained. The product is an isomer mixture in which the cis-cyclohexylamino derivative predominates.

4-Isopropenylcyclohexanone 4.1 g of a 37% strength solution of HF in trimethylamine were added dropwise with stirring at room temperature to 8.0 g (0.038 mol) of 1-trimethylsilyloxy-4-isopropenyl-1-cyclohexene in 100 ml of $CH_2Cl_2$, and the mixture was subsequently stirred for 2 hours. Water was added, extraction was carried out with $CH_2Cl_2$, and the combined organic phases were dried and concentrated. 4.7 g (90% of theory) were obtained of a colorless oil which was reacted without further purification.

1-Trimethylsilyloxy-4-isopropenyl-1-cyclohexene

From 23.5 g (0.066 mol) of methyltriphenylphosphonium bromide and 6.9 g (0.061 mol) of potassium tert-butylate, in 80 ml of ether at room temperature, the ylide was formed. To this solution were added dropwise at from 20° to 30° C. 10.0 g (0.047 mol) of 1-trimethylsilyloxy-4-acetyl-1-cyclohexene (Org. Synth. Coll. Vol. VI, 445) dissolved in 20 ml of ether. The mixture was stirred at room temperature for 3 hours. Water was then added, and extraction was carried out with ether. A spatula tip of hydroquinone was added to the combined ether phases, which were then dried and concentrated. The residue was extracted by stirring with heptane and the combined heptane phases were concentrated. 8.0 g (81% of theory) were obtained of a colorless oil which was reacted further without purification.

EXAMPLE 8

The following compound was prepared analogously to Example 7:

5-Chloro-6-ethyl-4-[cis-4-(2-penten-2-yl)cyclohexylamino]pyrimidine (E/Z mixture) (colorless oil)

EXAMPLE 9

4-(cis-4Isopropenylcyclohexyloxy)quinazoline 0.42 g (17.5 mmol) of NaH (80% pure) was added in portions to a solution of 1.8 g (12.8 mmol) of cis-4isopropenylcyclohexanol in 20 ml of absolute THF. The mixture was then heated at reflux for 3 hours, and a solution of 1.9 g (11.6 mmol) of 4-chloroquinazoline in 10 ml of THF was added dropwise. The reaction mixture was subsequently heated at reflux for 5 hours. After cooling to room temperature, 10 ml of isopropanol were added, the mixture was subsequently stirred for 15 minutes, and the reaction solution was poured into saturated ammonium chloride solution. Extraction was carried out with ether, the combined organic phases were dried over $MgSO_4$ and the solvent was concentrated by evaporation in vacuo. The residue (2.7 g) was purified by flash chromatography over silica gel with petroleum ether/ethyl acetate 3:1. After concentration, 1.8 g (57.6% of theory) were obtained of a colorless oil.

Preparation of the precursor cis-4-isopropenylcyclohexanol 4.7 g (0.034 mol) of 4-isopropenylcyclohexanone dissolved in 35 ml of THF were added dropwise to 39 ml of a 1 molar solution at −78° C. of L-Selectride in THF. The mixture was subsequently stirred at −78° for 3 hours and then heated to room temperature, and 5 ml of $H_2O$, 20 ml of ethanol, 15 ml of 6N NaOH and 17 ml of 35% strength $H_2O_2$ solution were added in succession. Water was added to the reaction solution, and extraction was carried out with methylene chloride. The combined methylene chloride phases are dried and concentrated. 37 g (78% of theory) of product remained as a colorless oil. The cis/trans mixture produced (>90% cis) was reacted further without additional purification.

the following compounds were prepared analogously to Example 9:

EXAMPLE 10

4-(cis-4-Isopropenylcyclohexyloxy)-5,6,7,8-tetrahydroquinazoline (colorless oil)

EXAMPLE 11

4-[cis-4-(1-Methylbut-1-enyl)cyclohexyloxy]quinazoline (E/Z mixture) (colorless oil)

EXAMPLE 12

5-(Chloro-4-(cis-4-ethenylcyclohexylamino)-6-ethylpyrimidine 66.7 g (187 mmol) of methyltriphenylphosphonium bromide were added in portions at 0° C. to a solution of 25.15 g (224 mmol) of potassium tert-butoxide in 80 ml of THF. After 10 minutes, 20.0 g (75 mmol) of 5-chloro-6-ethyl-4-(cis-4-formylcyclohexylamino)pyrimidine dissolved in 80 ml of THF were added dropwise at 0° C., and stirring was continued for 1 hour at the temperature indicated. The mixture was partitioned between dichloromethane and water, the aqueous phase was extracted with dichloromethane, and column chromatography on silica gel (eluent system petroleum ether/ethyl acetate 4:1) gave 14.5 g (72% of theory) of the vinyl compound as a colorless oil, $n_D^{23}$=1.5504.

Preparation of the precursor 5-chloro-6-ethyl-4-(cis-4-formylcyclohexylamino)pyrimidine 6.7 g (86 mmol) of DMSO in 17 ml of dichloromethane were added under $N_2$ to a solution of 5.5 g (43 mmol) of oxalyl chloride in 50 ml of dichloromethane at −78° C. After 5 minutes, a solution of 10.6 g (39 mmol) of the hydroxymethyl compound from Example 3 in 5.3 ml each of DMSO and dichloromethane was added, and the mixture was stirred for 1 hour at the temperature indicated. 35.6 g (350 mmol) of triethylamine were added dropwise. After 20 minutes, the mixture was allowed to warm to room temperature, 105 ml of $H_2O$ were added, extraction was carried out with dichloromethane, and removal of the solvent gave 9.5 g (35.5 mmol =91%) of the aldehyde as a white solid: m.p. 96° to 97° C.

The following compounds were prepared analogously to Example 12:

EXAMPLE 13

5-Chloro-6-ethyl-4-[trans-4-(1-propenyl)cyclohexylamino]pyrimidine (colorless oil)

EXAMPLE 14

5-Chloro-6-ethyl-4-[cis-4-(1-propenyl)cyclohexylamino]pyrimidine (colorless oil)

EXAMPLE 15

5-Chloro-6-ethyl-4-[cis-4-(2-bromoethenyl)cyclohexylamino]pyrimidine (colorless oil)

EXAMPLE 16

4-[cis-4-(1-methylcyclopropyl)cyclohexylamino]-5-chloro-6-ethylpyrimidine 1.8 g (13.0 mmol) of $K_2CO_3$ were placed in 10 ml of dimethylformamide, 1.3 g (8.5 mmol) of cis-4-(1-methylcyclopropyl)cyclohexylamine and 1.5 g (8.5 mmol)

of 4,5-dichloro-6-ethylpyrimidine were added, and the mixture was stirred at 80° C. for 4 hours. For working up, the cooled reaction solution was taken up in water. Extraction was carried out with ether, and the combined organic phases were washed with water, dried and concentrated. For purification, the mixture was chromatographed on silica gel with petroleum ether/ethyl acetate 3:1. 1.8 g (71.1% of theory) were obtained of a colorless oil.

Preparation of the precursors cis-4-(1-Methylcyclopropyl)cyclohexylamine 11.0 g (72.3 mmol) of 4-(1-methylcyclopropyl)cyclohexanone were stirred for 24 hours with 7.0 g (410 mmol) of $NH_3$ dissolved in 120 ml of methanol, in the presence of 3.0 g of Rh/C (5%) at a hydrogen pressure of 20 bar and at a reaction temperature of 50° C. The reaction solution was filtered and the filtrate was concentrated. 9.8 g (88% of theory) were obtained of a colorless oil which was reacted without further purification.

4-(1-Methylcyclopropyl)cyclohexanone 5.0 g (0.036 mol) of 4-isopropenylcyclohexanone (precursor to Example 4) were placed under inert gas in 150 ml of hexane, and 16.5 g (0.134 mol) of diethylzinc (1M in hexane) followed by 58.0 g (0.22 mol) of diiodomethane were added dropwise at −20° C. The mixture was stirred at −60° C. for 2 hours and then at 0° C. for 6 hours. The reaction solution was kept in a refrigerator overnight and was worked up by pouring it into cold $NH_4Cl$ solution and carrying out extraction with ether. The organic phase was washed with sodium thiosulfate solution and water, dried and concentrated. 5.3 g (96% of theory) of a colorless oil were obtained which was reacted without further purification.

The following compounds were prepared analogously to Example 16:

EXAMPLE 17

4[cis-4-(1-Methylcyclopropyl)cyclohexylamino]quinazoline colorless crystals, m.p.: 107° to 108° C.

EXAMPLE 18

5-Bromo-6-ethyl-4-[cis-4(1-methylcyclopropyl)cyclohexylamino]pyrimidine colorless oil

EXAMPLE 19

5-Methoxy-6-methoxymethyl-4-[cis-4-(1-methylcyclopropyl)cyclohexylamino]pyrimidine colorless oil

EXAMPLE 20

4-[cis-4-(1-Methylcyclopropyl)cyclohexyloxy]quinazoline 0.32 g (10.8 mmol) of sodium hydride (80% dispersion in mineral oil) was added to a solution of 1.7 g (7.9 mmol) of cis-4-(1-methylcyclopropyl)cyclohexanol in 20 ml of tetrahydrofuran, and the mixture was heated under reflux for 3 hours. It was then cooled to room temperature, 1.2 g (7.2 mmol) of 4-chloroquinazoline dissolved in 5 ml of tetrahydrofuran were added, and the mixture was heated under reflux for 2 hours. After cooling to room temperature, isopropanol was added to the reaction solution, which was subsequently stirred for 15 minutes and poured into water, after which extraction was carried out with diethyl ether. The organic phase was dried and concentrated. The residue was purified by chromatography on silica gel with petroleum ether/ethyl acetate 3:1. 1.2 g (62% of theory) were obtained of a colorless oil, which gradually solidified.

the following compound was prepared analogously:

EXAMPLE 21

4[cis-4-(1-Methylcyclopropyl)cyclohexyloxy]-5,6,7,8-tetrahydroquinazoline colorless oil Preparation of the precursor cis-4-(1-methylcyclopropyl)cyclohexanol A solution of 4.0 g (26.3 mmol) of 4-(1-methylcyclopropyl)cyclohexanone in 30 ml of THF was added dropwise at −78° C. to 5.5 g (29.0 mmol) of L-Selectride (1M in THF) and the mixture was subsequently stirred for 3 hours. It was then heated to room temperature, and 4 ml of $H_2O$, 15 ml of ethanol, 11 ml of 6N NaOH and 13 ml of 35% strength $H_2O_2$ solution were added in succession to the reaction solution. This solution was left to stand overnight and then subjected to aqueous workup. Extraction was carried out with methylene chloride, and the extract was dried and concentrated. 3.4 g (86% of theory) were obtained of a colorless crystal powder, m.p.: 56° to 57° C.

EXAMPLE 22

5-Methoxy-6-methoxymethyl-4-[cis-4-(1-methylcyclohexyl)cyclohexylamino]pyrimidine 2.83 g (15 mmol) of 4-chloro-5-methoxy-6-methoxymethylpyrimidine [Collection Czechoslov. Chem. Commun. 33 (1968) 2266], 2.93 g (15 mmol) of cis-4-(1-methylcyclohexyl)cyclohexylamine and 3.03 g (30 mmol) of triethylamine are heated under reflux in 10 ml of toluene for 6 hours. After cooling, the mixture was subjected to extraction by stirring with water, and the organic phase was dried and concentrated. For purification it was chromatographed on silica gel (eluent: ethyl acetate). 1.2 g (23% of theory) of pure cis isomer were obtained as a colorless oil.

Preparation of the precursors:

cis-4-(1-Methylcyclohexyl)cyclohexylamine 36 g (0.185 mol) of 4-(1-methylcyclohexyl)cyclohexanone were subjected to reductive amination in 210 ml of ammonia-saturated methanol in the presence of 3 g of rhodium (5% on charcoal) at 50° C. and 50 bar hydrogen pressure.

26.5 g (73% of theory) were obtained of a colorless oil which was reacted without further purification.

4-(1-Methylcyclohexyl)cyclohexanone

A solution of 23 g of sodium dichromate in a mixture of 19 ml of concentrated sulfuric acid and 65 ml of water was added dropwise at from 15° to 20° C. to a solution of from 45.8 g (0.23 mol) of 4-(1-methylcyclohexyl)cyclohexanol in 900 ml of acetone. The mixture was stirred at room temperature for one hour, 150 ml of isopropanol were added, stirring was continued for 15 minutes, and the inorganic material was filtered off with suction. The filtrate was brought to a pH of from 6.5 to 7 with solid sodium bicarbonate and then the mixture was filtered again. The filtrate was concentrated, the residue was taken up in toluene/water, and the organic phase was dried and concentrated.

Vacuum distillation gave 36 g (80% of theory) of a colorless oil which gradually solidified. m.p.: 46° to 47° C.

cis-4-(1-Methylcyclohexyl)cyclohexanol 56.1 g (0.29 mol) of 4-(1-methylcyclohexyl)phenol (from 1-methylcyclohexene and phenol in accordance with Chem. Ber. 57 (1924) 857) in 200 ml of methanol to which 1 ml of concentrated hydrochloric acid had been added were hydrogenated at 50° C. with 150 bar of hydrogen in the presence of 5 g of rhodium (5% on charcoal). After removal of the catalyst by filtration with suction, and concentration, 56.1 g (98.5% of theory) remained of an almost pure cis alcohol as a colorless solid.

The following compounds were prepared analogously to Example 22:

EXAMPLE 23

4[cis-4-(1-Methylcyclohexyl)cyclohexylamino] quinazoline colorless crystals, m.p.: 113° to 114° C.

EXAMPLE 24

5-Bromo-6-ethyl-4-[cis-4-(1-methylcyclohexyl) cyclohexylamino]pyrimidine colorless oil

EXAMPLE 25

5-Chloro-6-ethyl-4-[cis-4-(methylcyclohexyl) cyclohexylamino]pyrimidine

EXAMPLE 26

4-[cis-4-(1-Methylcyclohexyl)cyclohexyloxy] quinazoline 1.47 g (7.5 mmol) of cis-4-(1-methylcyclohexyl) cyclohexanol (Example 22) and 300 mg (10 mmol) of sodium hydride (80% in oil) were heated at 50° C. in 10 ml of tetrahydrofuran until the end of evolution of hydrogen. 1.23 g (7.5 mmol) of 4-chloroquinazoline were added and the mixture was heated under reflux for 8 hours. It was diluted with toluene and subjected to extraction by stirring with water. The organic phase was dried and concentrated. The residue was purified by chromatography on silica gel (eluent: petroleum ether/ethyl acetate 7:3). A colorless oil was obtained. For further purification it was taken up in ether and the hydrochloride was precipitated with ethereal hydrochloric acid. The end product was obtained as a free base from this hydrochloride with sodium hydroxide solution. Yield 0.82 g (33.7% of theory) of colorless crystals, m.p.: 77° to 78° C.

EXAMPLE 27

5-Methoxy-6-methoxymethyl-4-[cis-4-(1-methylcyclopentyl)cyclohexylamino]pyrimidine colorless oil The compound was obtained entirely in analogy to Example 22, starting from phenol and 1-methylcyclohexene (colorless oil).

the following compounds were prepared analogously:

EXAMPLE 28

5-Chloro-6-ethyl-4-[cis-4-(1-methylcyclopentyl) cyclohexylamino]pyrimidine colorless oil

EXAMPLE 29

5-Bromo-6-ethyl-4-[cis-4-(1-methylcyclopentyl) cyclohexylamino]pyrimidine colorless oil

EXAMPLE 30

4-[cis-4-(1-methylcyclopentyl)cyclohexylamino] quinazoline colorless crystals, m.p.: 118° to 119° C.

EXAMPLE 31

5-Chloro-6-ethyl-4-[cis-4-(1-methyl-1-silacyclopentyl)cyclohexylamino]pyrimidine Prepared analogously to Example 22 from 1.2 g (6.8 mmol) of 4,5-dichloro-6-ethylpyrimidine, 1.5 g (7.6 mmol) of 1-amino-4-(1-methyl-1-silacyclopentyl)cyclohexane (prepared analogously to the synthesis of 4-trimethylsilylcyclohexylamine, DE-A 19511562, J. Amer. Chem. Soc. 76 (1954) 6012) and 2.0 g of triethylamine in 10 ml of toluene. Chromatography of the crude product on silica gel with petroleum ether/ethyl acetate 9:1 gave in addition to 0.1 g (4.4% of theory) of trans product (resin) 1.1 g (47.9% of theory) of cis isomer (colorless resin).

the following compounds were prepared analogously:

EXAMPLE 32

4-[cis-4-(1-Methyl-silacyclopentyl) cyclohexylamino]quinazoline colorless crystals, m.p.: 142° to 143° C.

EXAMPLE 33

5-Bromo-6-ethyl-4-[cis-4-(1-methyl-1-silacyclopentyl)cyclohexylamino]pyrimidine

EXAMPLE 34

5-Methoxy-6-methoxymethyl-4-[cis-4-(1-methyl-1-silacyclopentyl)cyclohexylamino]pyrimidine colorless oil

EXAMPLE 35

5-Chloro-6-ethyl-4-[cis-4-(1-methyl-1-silacyclopentyl)cyclohexylamino]pyrimidine colorless oil

EXAMPLE 36

5-Bromo-6-ethyl-4-[cis-4-(1-methyl-1-silacyclohexyl)cyclohexylamino]pyrimidine colorless oil

EXAMPLE 37

5-Methoxy-6-methoxymethyl-4-[cis-4-(1-methyl-1-silacyclohexyl)cyclohexylamino]pyrimidine

EXAMPLE 38

4-[cis-4-(1-Methyl-1-silacyclohexyl) cyclohexylamino]quinazoline (colorless resin)

EXAMPLE 39

5-Bromo-6-ethyl-4-[cis-4-[(2-ethoxyethyl)silyl]cyclohexylaminopyrimidine

Prepared analogously to Example 31 from 0.97 g (4.4 mmol) of 5-bromo-4-chloro-6-ethylpyrimidine, 1.00 g (4.4 mmol) of 1-amino-4-[dimethyl(2-ethoxyethyl)silyl]cyclohexane (prepared analogously to the synthesis of 4-trimethylsilylcyclohexylamine, DE-A 19511562, Helv. Chim. Acta 59 (1976) 717) and 15 ml of triethylamine as solvent and auxiliary base. Chromatography on silica gel with petroleum ether/ethyl acetate 7:3 gave 0.68 g (37.3% of theory) of product as a colorless oil.

The compounds listed in Table 1 were synthesized analogously to Example 39.

TABLE 1

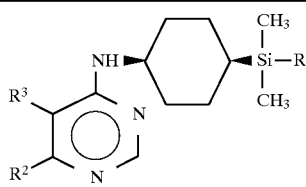

| Ex. No. | $R^2$ | $R^3$ | R | Refractive index at 22° C. | m.p. (°C.) |
|---|---|---|---|---|---|
| 40 | $C_2H_5$ | Cl | $-(CH_2)_2OC_2H_5$ | 1.5205 | oil |
| 41 | $CH_2OCH_3$ | $OCH_3$ | $-(CH_2)_2OC_2H_5$ | 1.5153 | oil |
| 42 | $-CH=CH-CH=CH-$ | | $-(CH_2)_2OC_2H_5$ | | 69–70 |
| 43 | $C_2H_5$ | $(CH_3)_2Si-C\equiv C-$ | $-(CH_2)_2OC_2H_5$ | | resin |
| 44 | $C_2H_5$ | $HC\equiv C-$ | $-(CH_2)_2OC_2H_5$ | | resin |
| 45 | $C_2H_5$ | I | $-(CH_2)_2OC_2H_5$ | | resin |
| 46 | $C_2H_5$ | $OCH_3$ | $-(CH_2)_2OC_2H_5$ | | resin |
| 47 | $C_2H_5$ | $OC_2H_5$ | $-(CH_2)_2OC_2H_5$ | | resin |
| 48 | $C_2H_5$ | H | $-(CH_2)_2OC_2H_5$ | | resin |
| 49 | $C_2H_5$ | Cl | $(CH_2)_3O(CH_2)_2OCH_3$ | 1.5172 | resin |
| 50 | $C_2H_5$ | Br | $(CH_2)_3O(CH_2)_2OCH_3$ | | resin |
| 51 | $-CH=CH-CH=CH-$ | | $(CH_2)_3O(CH_2)_2OCH_3$ | 1.5609 | resin |
| 52 | $CH_2OCH_3$ | $OCH_3$ | $(CH_2)_3O(CH_2)_2OCH_3$ | 1.5122 | resin |
| 53 | $C_2H_5$ | Cl | $(CH_2)_3O(CH_2)_2OC_2H_5$ | 1.5138 | resin |
| 54 | $C_2H_5$ | Br | $(CH_2)_3O(CH_2)_2OC_2H_5$ | 1.5162 | resin |
| 55 | $CH_2OCH_3$ | $OCH_3$ | $(CH_2)_3O(CH_2)_2OC_2H_5$ | 1.5079 | resin |
| 56 | $-CH=CH-CH=CH-$ | | $(CH_2)_3O(CH_2)_2OC_2H_5$ | 1.5461 | resin |
| 57 | $C_2H_5$ | $OCH_3$ | $(CH_2)_3O(CH_2)_2OC_2H_5$ | 1.5097 | resin |
| 58 | $C_2H_5$ | H | $(CH_2)_3O(CH_2)_2OC_2H_5$ | | resin |
| 59 | $C_2H_5$ | Cl | $(CH_2)_3OC_2H_5$ | | resin |
| 60 | $C_2H_5$ | Br | $(CH_2)_3OC_2H_5$ | | resin |
| 61 | $C_2H_5$ | Cl | $(CH_2)_3-O-\text{cyclohexyl}$ | | resin |
| 62 | $C_2H_5$ | Br | $(CH_2)_3-O-\text{cyclohexyl}$ | | resin |
| 63 | $C_2H_2OCH_3$ | $OCH_3$ | $(CH_2)_3-O-\text{cyclohexyl}$ | | resin |
| 64 | $-CH=CH-CH=CH-$ | | $(CH_2)_3-O-\text{cyclohexyl}$ | | resin |
| 65 | $C_2H_5$ | Cl | $-(CH_2)_3O(CH_2CH_2O)_2C_2H_5$ | 1.5099 | resin |
| 66 | $C_2H_5$ | Br | $-(CH_2)_3O(CH_2CH_2O)_2C_2H_5$ | 1.5169 | resin |
| 67 | $CH_2OCH_3$ | $OCH_3$ | $-(CH_2)_3O(CH_2CH_2O)_2C_2H_5$ | 1.5048 | resin |
| 68 | $C_2H_5$ | $OCH_3$ | $-(CH_2)_3O(CH_2CH_2O)_2C_2H_5$ | 1.5073 | resin |
| 69 | $-CH=CH-CH=CH-$ | | $-(CH_2)_3O(CH_2CH_2O)_2C_2H_5$ | 1.5462 | resin |
| 70 | $C_2H_5$ | Cl | $(CH_2)_3O(CH_2)_2OCH(CH_3)_2$ | 1.5067 | resin |
| 71 | $C_2H_5$ | Br | $(CH_2)_3O(CH_2)_2OCH(CH_3)_2$ | 1.5139 | resin |
| 72 | $CH_2OCH_3$ | $OCH_3$ | $(CH_2)_3O(CH_2)_2OCH(CH_3)_2$ | 1.5048 | resin |
| 73 | $-CH=CH-CH=CH-$ | | $(CH_2)_3O(CH_2)_2OCH(CH_3)_2$ | 1.5429 | resin |
| 74 | $C_2H_5$ | $OCH_3$ | $(CH_2)_3O(CH_2)_2OCH(CH_3)_2$ | 1.5070 | resin |

TABLE 1-continued

[Structure: pyrimidine ring with R² and R³ substituents, NH linked to cyclohexyl bearing Si(CH₃)₂-R group]

| Ex. No. | R² | R³ | R | Refractive index at 22° C. | m.p. (°C.) |
|---|---|---|---|---|---|
| 75 | $C_2H_5$ | Cl | $(CH_2)_3O(CH_2)_2OCH(CH_3)_2$ | | resin |
| 76 | $C_2H_5$ | Br | $(CH_2)_3O(CH_2)_2OCH(CH_3)_2$ | | resin |
| 77 | $CH_2OCH_3$ | $OCH_3$ | $(CH_2)_3O(CH_2)_2OCH(CH_3)_2$ | | resin |
| 78 | $C_2H_5$ | $OCH_3$ | $(CH_2)_3O(CH_2)_2OCH(CH_3)_2$ | 1.5070 | resin |
| 79 | —CH=CH—CH=CH— | | $(CH_2)_3O(CH_2)_2OCH(CH_3)_2$ | 1.5490 | resin |

EXAMPLE 80

4-[4cis-(1-Cyclohexyl-2,2,2-trifluoro-1-trifluoromethylethyl)cyclohexyloxy]quinazoline 0.22 g (7.3 mmol) of sodium hydride (80% dispersion in mineral oil) was added to 2.0 g (6.1 mmol) of cis-4-(1-cyclohexyl-2,2,2-trifluoro-1-trifluoromethylethyl)cyclohexanol in 30 ml of dry tetrahydrofuran, and the mixture was heated at 50° C. for 3 hours. After cooling to room temperature, 1.1 g (6.6 mmol) of 4-chloroquinazoline were added, and the mixture was heated with stirring for 6 hours. After cooling to room temperature, 3 ml of isopropanol were added, the mixture was concentrated to dryness, and the residue was taken up in water/dichloromethane. The organic phase was dried and concentrated and the residue was purified by chromatography on silica gel (eluent petroleum ether/ethyl acetate 7:3). 1.9 g (68% of theory) were obtained of a colorless solid, m.p.: 107° to 108° C.

The following compounds were obtained analogously:

EXAMPLE 81

4-[cis-4-(1-Cyclohexyl-2,2,2-trifluoro-1-trifluoromethylethyl)cyclohexyloxy]-5,6,7,8-tetrahydroquinazoline; m.p. 114° to 115° C.

EXAMPLE 82

5-Chloro-6-ethyl-4-[cis-4-(1-cyclohexyl-2,2,2-trifluoro-1-trifluoromethylethyl)cyclohexyloxy]pyrimidine; m.p. 58° to 59° C.

EXAMPLE 83

5-Methoxy-6-methoxymethyl-4-[cis-4-(1-cyclohexyl-2,2,2-trifluoro-1-trifluoromethylethyl)cyclohexyloxy]pyrimidine; colorless oil Preparation of the starting alcohol cis-4-(1-cyclohexyl-2,2,2-trifluoro-1-trifluoromethylethyl)cyclohexanol The alcohol was obtained by catalytic hydrogenation (100°/100 bar/Rh catalyst) of 4-(2,2,2-trifluoro-1-phenyl-1-trifluoromethylethyl)phenol in methanol with the addition of a little concentrated hydrochloric acid.

EXAMPLE 84

5-Chloro-6-ethyl-4-[cis-4-( 1-cyclohexyl-2,2,2-trifluoro-1-trifluoromethylethyl)cyclohexylamino]pyrimidine 2.0 g (6 mmol) of cis-4-(1-cyclohexyl-2,2,2-trifluoro-1-trifluoromethylethyl)cyclohexylamine, 1.1 g (6.00 mmol) of 4,5-dichloro-6-ethylpyrimidine and 1.2 g (12 mmol) of triethylamine were stirred at 90° C. without solvent for 6 hours. The mixture was taken up in water/dichloromethane, and the organic phase was dried and concentrated. Chromatography on silica gel with petroleum ether/ethyl acetate gave 1.3 g (46% of theory) of a colorless oil.

Preparation of the starting amine cis-4-(1-cyclohexyl-2,2,2-trifluoro-1-trifluoromethylethyl)cyclohexylamine The alcohol cis-4-(bistrifluoromethylcyclohexylmethyl)cyclohexanol described as starting material for Examples 80 to 83 was oxidized to the corresponding cyclohexanone using Jones' reagent ($CrO_3/H_2SO_4$) in acetone (analogously to Org. Synth. Coll. Vol. V, 310), and this cyclohexanone was converted to the cyclohexylamine by reductive amination ($H_2/NH_3$/rhodium, 100°/100 bar, methanol as solvent). In this conversion, almost exclusively the cis isomer was obtained.

EXAMPLE 85

4-(cis-4-Cyanocyclohexylamino)-5-chloro-6-ethylpyrimidine 4.1 g (10 mmol) of trans-4-(5-chloro-6-ethylpyrimidin-4-ylamino)cyclohexane p-toluenesulfonate and 20 ml of lithium cyanide solution (0.5M solution in dimethylformamide) were stirred at room temperature for 2 hours and at 100° C. for 6 hours. The solvent was stripped off in vacuo, the residue was taken up in water/dichloromethane, and the crude product was chromatographed on silica gel with petroleum ether/ethyl acetate 1:1. The initial product was a mixed fraction consisting of a little starting material and the elimination product 5-chloro-6-ethyl-4-(cyclohex-1-en-4-ylamino)pyrimidine (m.p. 91° to 92° C.), followed by 0.3 g (11% of theory) of the desired product. colorless crystals, m.p. 131° to 132° C.

Preparation of the starting compound trans-4-(5-Chloro-6-ethylpyrimidine-4-ylamino)cyclohexane p-toluenesulfonate 11.0 g (43 mmol) of trans-4-(5-chloro-6-ethylpyrimidin-4-ylamino)cyclohexanol were dissolved in 50 ml of pyridine, and 8.2 g (43 mmol) of p-toluenesulfonyl chloride were introduced in portions at 0° C. The mixture was stirred at room temperature for 6 hours, poured onto ice, acidified with concentrated hydrochloric acid to a pH of 3 to 4 and subjected to extraction with dichloromethane. After drying of the organic phase and removal of the solvent by stripping, 14.4 g (81.7% of theory) remained of a colorless solid, m.p. 142° to 144° C.

The trans-4-(5-chloro-6-ethylpyrimidin-4-ylamino) cyclohexanol required for the above reaction was obtained by two methods:

a.) $NaBH_4$ reduction of 4(4chloro-6-ethylpyrimidin-4-ylamino)cyclohexanone (preparation: DE-A-44 17 163)

b.) Reaction of 4,5-dichloro-6-ethylpyrimidine with 4-aminocyclohexanol in the presence of triethylamine analogously to Example 83 m.p. 140° to 141° C.

EXAMPLE 86

5-Chloro-6-ethyl-4-[cis-4-(2-triethylsilylethyl)cyclohexylamino] pyrimidine 2.0 g (7.3 mmol) of 5-chloro-4-(cis-4-ethenylcyclohexylamino)-6-ethylpyrimidine (Example 12) and 1.22 g (10.5 mmol) of triethylsilane were heated under reflux with a spatula tip of hexachloroplatinic acid. After hydrolysis with dilute $NH_4Cl$ solution, the mixture was subjected to extraction with ether and purified by column chromatography (silica gel, eluent system petroleum ether/ethyl acetate 9:1). 0.72 g (1.9 mmol=25%) was obtained of the silane (colorless oil, $n_D^{23}$=1.5206).

EXAMPLE 87

4-[cis-4-(2-hydroxy-1,1,1-trifluoropropyl) cyclohexyloxy]quinazoline

The compound was synthesized analogously to Example 9 from 4chloroquinazoline and cis-4-(2-hydroxy- 1,1,1-trifluoropropyl)cyclohexanol (Example 2) in the presence of 2 equivalents of sodium hydride. colorless crystals, m.p.: 159° to 160° C.

The following compounds were prepared analogously to Example 87:

EXAMPLE 88

5-methoxy-6-methoxymethyl-4-[cis-4-(2-hydroxy-1,1,1-trifluoropropyl)cyclohexyloxy]pyrimidine colorless oil

EXAMPLE 89

4[cis-4-(2-hydroxy-1,1,1-trifluoropropyl) cyclohexyloxy]-5,6,7,8-tetrahydroquinazoline colorless crystals, m.p.: 88° to 90° C.
We claim:
1. A compound of the formula I

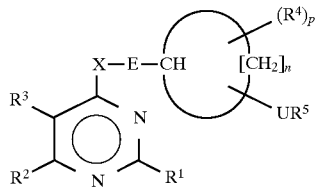

in which
$R^1$ is hydrogen, halogen, $(C_1-C_4)$-alkyl, $(C_1-C_4)$-haloalkyl, $(C_3-C_5)$-cycloalkyl or halo-$(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_8)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_{1-4})$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or $R^2$ and $R^3$, together with the carbon atoms to which they are attached, form an unsaturated 5- or 6-membered carbocyclic ring which, if it is a 5-membered ring, a $CH_2$ group is optionally replaced by an oxygen or sulfur atom or, if it is a 6-membered ring, one or two $CH_2$ groups are optionally replaced by one or two nitrogen atoms and which is unsubstituted or substituted by 1,2 or 3 identical or different radicals which are $(C_1-C_4)$-alkyl, $(C_1-C_4)$-haloalkyl, halogen, $(C_1-C_4)$-alkoxy or $(C_1-C_4)$-haloalkoxy; or by 1,2 or 3 identical or different radicals which are $(C_1-C_4)$-alkyl, $(C_1-C_4)$-haloalkyl, halogen, $(C_1-C_4)$-alkoxy or $(C_1-C_4)$-haloalkoxy; or $R^2$ and $R^3$, together with the carbon atoms to which they are attached, form a saturated 5-, 6- or 7-membered carbocyclic ring in which one or two $CH_2$ groups of said carbocyclic ring are optionally replaced by an oxygen or sulfur atom and which is unsubstituted or substituted by 1,2 or 3 $(C_1-C_4)$-alkyl groups;

X is NH, oxygen or $S(O)_q$ where q=0,1 or 2;

E is a direct bond or a straight-chain or branched $(C_1-C_4)$-alkanediyl group;

n is an integer 2, 3, 4, 5 or 6;

$(R^4)_p$ and $UR_5$ are substituents of the carbocyclic ring formed with the participation of $[CH_2]_n$;

$R_4$ is hydrogen, halogen, alkyl, haloalkyl, alkoxy or alkylthio; and p is 1 or 2;

U is a direct bond, oxygen or a group $S(O)_m$ where m=0, 1 or 2;

$R^5$ is alkenyl if U is as defined above; or $R^5$ is alkyl if U is a group $S(O)_m$; or $R^5$ is aryl or heterocyclyl if U is a group $S(O)_m$, m is 1 or 2; or $R^5$ is heterocyclyl if U is oxygen; or $R^5$ is a haloalkyl group which if unsubstituted must contain more than 4 carbon atoms, if U is oxygen or a direct bond; or $R^5$ if U and A are as defined above is alkynyl, hydroxyalkyl, cyanoalkyl, cyano, nitro, nitroalkyl, thiocyano, thiocyanoalkyl, cycloalkoxyalkyl, cycloalkylalkoxyalkyl, aryloxyalkyl, arylalkoxyalkyl, heterocyclyloxyalkyl, heterocyclylalkoxyalkyl, alkylmercaptoalkyl, cycloalkylmercaptoalkyl, cycloalkylalkylmercaptoalkyl, arylmercaptoalkyl, arylalkylmercaptoalkyl, heterocyclylmercaptoalkyl, heterocyclylalkylmercaptoalkyl, a group

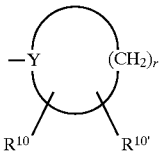

in which Y is carbon or silicon, r is an integer from 2 to 6 and $R^{10}$ and $R^{10'}$ are alkyl where, if Y is silicon, $R^{10}$ is optionally linked to Y; or is a group $R^6R^7R^8Si[(C_1-C_4)\text{-alkyl}]_s$ where s is zero or 1 and $R^6$ and $R^7$ are alkyl, and $R^8$ is mono-, di- or trioxaalkyl or cycloalkyl-oxa-alkyl and, if s is 1, is also alkyl, cycloalkyl, aryl or arylalkyl;

in which the aryl and heterocyclyl radicals and the radicals derived therefrom which are listed can be unsubstituted or provided with up to 3 identical or different radicals or, in the case of fluorine, up to the maximum number, and in the alkyl, haloalkyl, alkenyl, alkynyl or $(R^6R^7R^8Si)$-alkyl radicals mentioned one or more, non-adjacent saturated carbon units are optionally replaced by a heteroatom unit selected from the group consisting of oxygen, $S(O)_x$ where x=0, 1 or 2, $NR^9$ or $SiR^{6'}R^{7'}$, where $R^9$ is hydrogen, $(C_1-C_4)$-alkyl, $(C_1-C_4)$-alkanoyl or $(C_1-C_4)$-alkoxy and where $R^{6'}$ and $R^{7'}$ are $(C_1-C_4)$-alkyl, and in which, moreover, 3 to 12 atoms of these hydrocarbon or halogenated hydrocarbon radicals, unmodified or modified as above, optionally form a ring, and these hydrocarbon or halogenated hydrocarbon radicals, with or without the variations indicated are unsubstituted or substituted with one or more, identical or different substituents, in the case of halogen up to the maximum number, said substituents selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxy, cyano, thiocyano or nitro, where the cycloaliphatic, aromatic or heterocyclic ring systems of the substituents in this series is unsubstituted or substituted with up to three identical or different substituents, in the case of fluorine up to the maximum number, wherein in the definitions above, unless specified otherwise, aryl is an aromatic radical having 6 to 14 carbon atoms and heterocyclyl is a $C_3-C_8$ cycloalkyl ring in which a $CH_2$ group is replaced by O, S or $NR^{11}$ and $R^{11}$ is H, $C_1-C_8$ alkyl, $C_1-C_8$ alkoxy or is aryl or an aryl ring in which one of the CH groups is replaced by O, S, or N or is selected from the group consisting of thiazole, oxazole, imidazole, isothiazole, isoxazole, pyrazole, 1,3,4-oxadizole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzoxazole, benzothiazole, benzimidazole, benzisoxazole, benzisothiazole, benzopyrazole, benzothiadiazole, benzotriazole, pyrazine, pyrimidine, pyridazine, 1,3,5-triazine, 1,2,4-triazine, 1,2,4,5-tetrazine, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine; and wherein the substituents on the aliphatic aryl or heterocyclyl radicals, unless specified otherwise are selected from the group consisting of halogen, nitro, cyano, di-$(C_1-C_4)$-alkylamino, $(C_1-C_4)$-alkyl, $(C_3-C_8)$-cycloalkyl, $(C_1-C_4)$-trialkylsilyl, $(C_1-C_4)$-alkoxy, $(C_1-C_4)$-alkoxy-$(C_1-C_4)$-alkyl, $(C_1-C_2)$-alkoxy-$[CH_2-CH_2O]_{1,2}$-ethoxy, $(C_1-C_4)$-alkylthio, $(C_1-C_4)$-alkylsulfinyl, $(C_1-C_4)$-alkylsulfonyl, thiocyano, $(C_1-C_4)$-haloalkyl, $(C_1-C_4)$-haloalkoxy, $(C_1-C_4)$-haloalkylthio, $(C_2-C_4)$-haloalkylsulfinyl, $(C_1-C_4)$-haloalkylsulfonyl, $(C_2-C_4)$-alkenyl, $(C_2-C_4)$-haloalkenyl, trimethylsilylethynyl, $(C_1-C_4)$-alkanoyl, $(C_1-C_4)$-alkoxycarbonyl, phenyl, benzyl, phenoxy, halophenoxy, $(C_1-C_4)$-alkylphenoxy, $(C_1-C_4)$-alkoxyphenoxy, phenylthio, heterocyclyl, heterocyclylthio or heterocyclyloxy, where in the alkyl radicals and the radicals derived therefrom one or more hydrogen atoms, and in the case of fluorine up to the maximum number, are optionally replaced by halogen, and if these substituents are $(C_1-C_4)$-alkyl, they optionally are cyclically linked to form an indane, dihydroxynaphthyl, tetrahydronaphthyl or benzocycloheptane system, one or two aliphatic carbon units are optionally replaced by oxygen or sulfur and, on the aliphatic carbon atom units, one or more hydrogen atoms, and in the case of fluorine up to the maximum number, are optionally replaced by halogen or $(C_1-C_4)$-alkyl, or a salt thereof.

2. A compound as claimed in claim 1, in which $R^5$ is $(C_2-C_{20})$-alkenyl if U is as defined above; or $R^5$ is $(C_1-C_{20})$-alkyl if U is a group $S(O)_m$; or $R^5$ is aryl or heterocyclyl if U is a group $S(O)_m$, m is 1 or 2; or $R^5$ is heterocyclyl if U is oxygen; or $R^5$ is a $(C_1-C_{20})$-haloalkyl group which if unsubstituted must possess more than 4 carbon atoms, if U is oxygen or a direct bond; or $R^5$ is $(C_2-C_{20})$-alkynyl, $(C_1-C_{20})$-hydroxyalkyl, $(C_1-C_{20})$-cyanoalkyl, cyano, nitro, $(C_1-C_{20})$-nitroalkyl, thiocyano, $(C_1-C_{20})$-thiocyanoalkyl, $(C_3-C_8)$-cycloalkoxy-$(C_1-C_4)$-alkyl, $(C_3-C_8)$-cycloalkyl-$(C_1-C_4)$-alkoxy-$(C_1-C_4)$-alkyl, aryloxy-$(C_1-C_4)$-alkyl, aryl-$(C_1-C_4)$-alkoxy-$(C_1-C_4)$-alkyl, heterocycloxy-$(C_1-C_4)$-alkyl, heterocyclyl-$(C_1-C_4)$-alkoxy-$(C_1-C_4)$-alkyl, $(C_1-C_8)$-alkylmercapto-$(C_1-C_4)$-alkyl, $(C_3-C_8)$-cycloalkylmercapto-$(C_1-C_4)$-alkyl, $(C_3-C_8)$-cycloalkyl-$(C_1-C_4)$-alkylmercapto-$(C_1-C_4)$-alkyl, arylmercapto-$(C_1-C_4)$-alkyl, aryl-$(C_1-C_4)$-alkylmercapto-$(C_1-C_4)$-alkyl, heterocyclylmercapto-$(C_1-C_4)$-alkyl, heterocyclyl-$(C_1-C_4)$-alkylmercapto-$(C_1-C_4)$-alkyl, a group

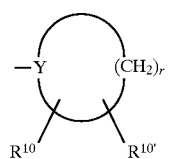

in which Y is carbon or silicon, r is an integer from 2 to 6 and $R^{10}$ and $R^{10'}$ are $(C_1-C_4)$-alkyl, in which, if Y is silicon, $R^{10}$ is optionally linked to Y; or is a group $R^6R^7R^8Si[(C_1-C_4)$-alkyl$]_s$, where s is zero or 1 and $R^6$ and $R^7$ are $(C_1-C_4)$-alkyl and $R^8$ is mono-, di- or trioxa-$(C_{1-20})$-alkyl or $(C_3-C_8)$-cycloalkyl-oxa-$(C_1-C_4)$-alkyl and, if s is 1, is also $(C_1-C_8)$-alkyl, $(C_3-C_8)$-cycloalkyl, aryl or aryl-$(C_1-C_4)$-alkyl;

in which the aryl and heterocyclyl radicals and the radicals derived therefrom which are listed are unsubstituted or provided with up to 3 identical or different radicals, or in the case of fluorine up to the maximum number and in the alkyl, haloalkyl, alkenyl, alkynyl or $(R^6R^7R^8Si)$-alkyl radicals mentioned, one or more, nonadjacent saturated carbon units are optionally replaced by heteroatom units selected from the group consisting of oxygen, $S(O)_x$ where x=0, 1 or 2, $NR^9$ or $SiR^{6'}R^{7'}$, in which $R^9$ is hydrogen, $(C_1-C_4)$-alkyl, $(C_1-C_4)$-alkanoyl or $(C_1-C_4)$-alkoxy, and where $R^{6'}$ and $R^{7'}$ are $(C_1-C_4)$-alkyl, and in which, moreover, 3 to 12 atoms of these hydrocarbon radicals or halogenated hydrocarbon radicals which are unmodified or are modified optionally form a ring and these hydrocarbon or halogenated hydrocarbon radicals, with or without the variations indicated are unsubstituted or substituted with one or more identical or different substituents, in the case of halogen up to the maximum number, said substituents being selected from the group consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_2)$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, where the cycloaliphatic, aromatic or heterocyclic ring systems among this series are unsubstituted or substituted with up to three identical or different substituents, and in the case of fluorine up to the maximum number, and, moreover, the groups —X—E— and $UR^5$, when n is 5, are cis to one another and take up positions 1 and 4 of the cyclohexane ring thus formed.

3. A compound as claimed in claim 1, in which $R^1$ is hydrogen, chlorine or fluorine;

$R^2$ is $(C_1-C_4)$-alkyl, $(C_1-C_4)$-haloalkyl, cyclopropyl, halocyclopropyl, $(C_2-C_4)$-alkenyl, $(C_2-C_4)$-haloalkenyl, $(C_2-C_4)$-alkynyl, trimethylsilylethynyl, methoxymethyl or cyano;

$R^3$ is hydrogen, halogen, methyl, ethyl, $(C_2-C_4)$-alkynyl, trimethylsilylethynyl, methoxy, ethoxy, cyano or $(C_1-C_4)$-alkoxycarbonyl; or $R^2$ and $R_3$, together with the carbon atoms to which they are attached, form an unsubstituted or substituted unsaturated carbocyclic 5- or 6-membered ring which,, if it is a 5-membered ring, a $CH_2$ group is optionally replaced a sulfur atom; or $R^2$ and $R^3$, together with the carbon atoms to which they are attached, form a saturated carbocyclic 5- or 6-membered ring in which a $CH_2$ group is optionally replaced by a sulfur atom or an oxygen atom;

X is NH or oxygen;

E is a direct bond;

n is the number 5;

$R^4$ is hydrogen, $(C_1-C_4)$-alkyl, trifluoromethyl or $(C_1-C_4)$-alkoxy; and, in addition, the groups —X—E— and $UR^5$ are in the 1- and 4-positions of the cyclohexane ring thus formed and are cis to one another.

4. A compound as claimed in claim 1, in which $R^1$ is hydrogen or fluorine;

$R^2$ is methyl, ethyl, propyl, isopropyl, $(C_1-C_2)$-fluoroalkyl, ethynyl, trimethylsilylethynyl, cyclopropyl or methoxymethyl;

$R^3$ is halogen, methyl, ethyl, ethynyl, trimethylsilylethynyl, methoxy, ethoxy or cyano; or $R^2$ and $R^3$, together with the ring system to which they are attached, form the quinazoline ring is optionally substituted in the carbocyclic part by fluorine; or $R^2$ and $R^3$, together with the carbon atoms to which they are attached, form a saturated carbocyclic 6-membered ring in which a $CH_2$ group is optionally replaced by an oxygen atom or sulfur atom; and $R^4$ is hydrogen, methyl or trifluoromethyl.

5. A compound as claimed in claim 1, in which $R^1$ is hydrogen;

$R^2$ is ethyl, propyl, isopropyl, trifluoromethyl, 1-fluoroethyl, ethynyl, trimethylsilylethynyl or methoxymethyl;

$R^3$ is fluorine, chlorine, bromine, ethynyl, trimethylsilylethynyl or methoxy;

$R^2$ and $R^3$, together with the ring system to which they are attached, form the quinazoline system which is optionally substituted with a fluorine atom; or $R^2$ and $R^3$, together with the ring system to which they are attached, form the 5, 6, 7, 8-tetrahydroquinazoline system;

X is NH or oxygen;

E is a direct bond;

$R^4$ is hydrogen or methyl;

n is the number 5;

and, in addition, the groups —X—E— and $UR^5$ are in the 1- and 4-positions of the cyclohexane ring thus formed and are cis to one another.

6. A compound as claimed in claim 1, in which $R^1$ is hydrogen;

$R^2$ is ethyl or methoxymethyl;

$R^3$ is fluorine, chlorine, bromine or methoxy; or $R^2$ and $R^3$, together with the ring system to which they are attached, form the quinazoline or 5, 6, 7, 8-tetrahydroquinazoline system;

X is NH or oxygen;

E is a direct bond;

$R^4$ is hydrogen;

n is the number 5;

U is a direct bond;

and, in addition, the groups —X—E— and $UR^5$ are in the 1- and 4-positions of the cyclohexane ring thus formed and are cis to one another.

7. A process for the preparation of a compound of the formula I as claimed in claim 1, which comprises reacting a compound of the formula II

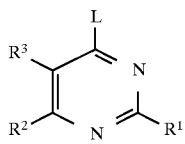

in which $R^1$, $R^2$ and $R^3$ are defined under formula I and L is a leaving group with a compound of the formula III

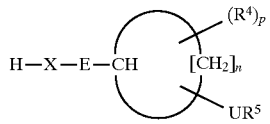

in which X, E, U, n, p, $R^4$ and $R^5$ are as defined under formula I and subjecting the compounds of the formula I obtained in this way to halogenation, optionally in position 5 of the heterocycle, or to further derivatization in the side chain $R^5$, and optionally converting the resulting compound, into a salt thereof.

8. A compound as claimed in claim 1, in which $R^1$ is hydrogen, halogen, $(C_1-C_4)$-alkyl; $(C_1-C_4)$-haloalkyl, $(C_3-C_5)$-cycloalkyl or halo-$(C_3-C_5)$-cycloalkyl;

$R^2$ is $(C_1-C_4)$-alkyl, $(C_1-C_4)$-haloalkyl, cyclopropyl, halocyclopropyl, $(C_2-C_4)$-alkenyl, $(C_2-C_4)$-haloalkenyl, $(C_2-C_4)$-alkynyl, trimethylsilylethynyl, methoxymethyl or cyano;

$R^3$ is hydrogen, halogen, methyl, ethyl, $(C_2-C_4)$-alkynyl, trimethylsilylethynyl, methoxy, ethoxy, cyano or $(C_1-C_4)$-alkoxycarbonyl; or X is NH;

E is a direct bond;

n is the number 5;

$R^4$ is $(C_1-C_{20})$ hydroxyalkyl and —X—E and $UR^5$ are in the 1- and 4-positions of the cyclohexane ring thus formed and are cis to one another.

9. A compound as claim in claim 1, in which $R^2$ is methoxymethyl and $R^3$ is methoxy, or $R^2$ is ethyl and $R^3$ is chlorine or bromine;

X is NH;

A is nitrogen;

or a salt thereof.

10. A compound as claimed in claim 1, which has the formula

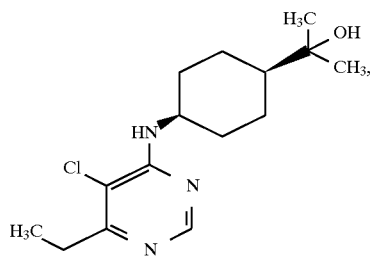

11. An insecticidal, acaricidal, ixodicidal or nematicidal composition, comprising an effective quantity of at least one compound as claimed in claim 1 together with the additives or auxiliaries customary for this application.

12. A method of controlling harmful insects, acarids, mollusks and nematodes, in which an effective quantity of a compound as claimed in claim 1 is applied to these pests or to the plants, areas or substrates infested by them.

* * * * *